US006440928B1

(12) United States Patent
Ishii

(10) Patent No.: US 6,440,928 B1
(45) Date of Patent: Aug. 27, 2002

(54) METHOD FOR TREATING DIABETIC NEUROPATHY WITH NGF

(75) Inventor: Douglas N. Ishii, LaPorte, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/004,965

(22) Filed: Jan. 8, 1998

Related U.S. Application Data

(63) Continuation of application No. 08/398,852, filed on Mar. 6, 1995, which is a continuation of application No. 07/909,200, filed on Jul. 6, 1992, now abandoned, which is a continuation-in-part of application No. 07/781,908, filed on Oct. 24, 1991, now abandoned, which is a continuation-in-part of application No. 07/280,557, filed on Dec. 6, 1988, now abandoned.

(51) Int. Cl.[7] .......................... C07K 38/18; C07K 38/30

(52) U.S. Cl. .............................. 514/2; 514/3

(58) Field of Search .......................... 514/2, 3; 530/350

(56) References Cited

U.S. PATENT DOCUMENTS

| | | | | |
|---|---|---|---|---|
| 4,652,583 A | * | 3/1987 | Mosnier et al. | 514/461 |
| 4,801,575 A | | 1/1989 | Pardridge | |
| 4,898,856 A | | 2/1990 | Aroonsakul | |
| 4,988,675 A | | 1/1991 | Froesch et al. | |
| 5,068,224 A | | 11/1991 | Fryklund et al. | |
| 5,093,317 A | | 3/1992 | Lewis et al. | |
| 5,407,927 A | | 4/1995 | Morales et al. | |
| 5,420,112 A | | 5/1995 | Lewis et al. | |
| 5,714,460 A | | 2/1998 | Gluckman et al. | 514/3 |
| 5,817,623 A | * | 10/1998 | Ishii | 514/3 |

FOREIGN PATENT DOCUMENTS

| | | |
|---|---|---|
| WO | WO90/14838 | 12/1990 |
| WO | WO93/02965 | 2/1993 |
| WO | WO93/08828 | 5/1993 |
| WO | WO95/13823 | 5/1995 |

OTHER PUBLICATIONS

Rich et al. (1987) J. Neurocytology 16:261–268, 1987.*
Budavari, S. et al. (eds.), *The Merck Index*, Twelfth Edition, Merck & Co., Rahway, N.J., pp. 1090–1091, 1112 (1996).
Budavari, S. et al. (eds.), *The Merck Index*, Eleventh Edition, Merck & Co., Rahway, N.J., pp. 1004, 1025 (1989).
Windholz, M. et al. (eds.), *The Merck Index*, Tenth Edition, Merck & Co., Rahway, N.J. pp. 910–911, 930 (1983).
Ullrich, A. et al., "Human β–Nerve Growth Factor Gene Sequence Highly Homologous to That of Mouse", Nature 303:821–825 (1983).
Barde, Y.–A., "Biological Roles of Neurotrophins", pp. 1–31 in *Handbook of Experimental Pharmacology*, Born, G.V.R. et al., eds. v.134 (1999).

Cohen, S. et al., "A Nerve Growth–Stimulating Factor Isolated from Sarcomas 37 and 180", Proc. Nat. Acad. Sci. USA 40:1014–1018 (1954).
Levi–Montalcini, R., et al., "Selective Growth Stimulating Effects of Mouse Sarcoma on the Sensory and Sympathetic Nervous System of the Chick Embryo", J. Exp. Zool. 116:321–361 (1951).
Levi–Montalcini, R., "Effects of Mouse Tumor Transplantation on the Nervous System", Ann. NY Acad. Sci. 55:330–344 (1952).
Cohen, S., "Purification and Metabolic Effects of a Nerve Growth–Promoting Protein from Snake Venom", J. Biol. Chem. 234:1129–1137 (1959).
Cohen, S., "Purification of a Nerve–Growth Promoting Protein from the Mouse Salivary Gland and its Neuro–Cytotoxic Antiserum", Proc. Nat. Acad. Sci. USA 46:302–311 (1960).
Varon, S. et al., "Reversible Dissociation of the Mouse Nerve Growth Factor Protein into Different Subunits", Biochem. 7:1296–1303 (1968).
Angeletti, R.H., and R. A. Bradshaw, "Nerve Growth Factor from Mouse Submaxillary Gland: Amino Acid Sequence", Proc. Nat. Acad. Sci. USA 68:2417–2420 (1971).
Scott, J. et al., "Isolation and Nucleotide Sequence of a cDNA Encoding the Precursor of Mouse Nerve Growth Factor", Nature 302:538–540 (1983).
McDonald, N. et al., "New Protein Fold Revealed by a 2.3A Resolution Crystal Structure of Nerve Growth Factor", Nature 354:411–414 (1991).
Harper, G.P., et al., "Guinea Pig Prostate is a Rich Source of Nerve Growth Factor", Nature 279:160–162 (1979).
Barker, P.A., and R.A. Murphy, "The Nerve Growth Factor Receptor: a Multicomponent System that Mediates the Actions of the Neurotrophin Family of Proteins", Mol. Cell. Biochem. 110:1–15 (1992).
Hefti, F. and P.A. Lapchak, "Pharmacology of Nerve Growth Factor in the Brain", pp. 239–272 in Advances in Pharmacology, August, J.T. et al., eds., Academic Press, San Diego, CA, v.24 (1993).
Raivich, G. and W. Kreutzberg, "Nerve Growth Factor and Regeneration of Peripheral Nervous System", Clin. Neurol. Neurosurg. 95(Suppl.): S84–S88 (1993).
Levi–Montalcini, R. and P.U. Angeletti, "Nerve Growth Factor", Physiol Rev. 48:534–569 (1968).
Thoenen, H, and Y.–A. Barde, "Physiology of Nerve Growth Factor", Physiol Rev. 60:1284–1335 (1980).
Levi–Montalcini, R., "The Nerve Growth Factor 35 Years Later", Science 237:1154–1162 (1987).
Bradshaw, R.A. et al., "Nerve Growth Factor Revisited", TIBS 18:48–52 (1993).

(List continued on next page.)

Primary Examiner—Michael Pak
(74) Attorney, Agent, or Firm—Howrey Simon Arnold & White, LLP

(57) ABSTRACT

Mammals suffering from diabetic neuropathy can be treated by a method involving administering to the mammal nerve growth factor (NGF) in an amount effective to ameliorate the diabetic neuropathic condition.

3 Claims, 9 Drawing Sheets

OTHER PUBLICATIONS

Figure 1:
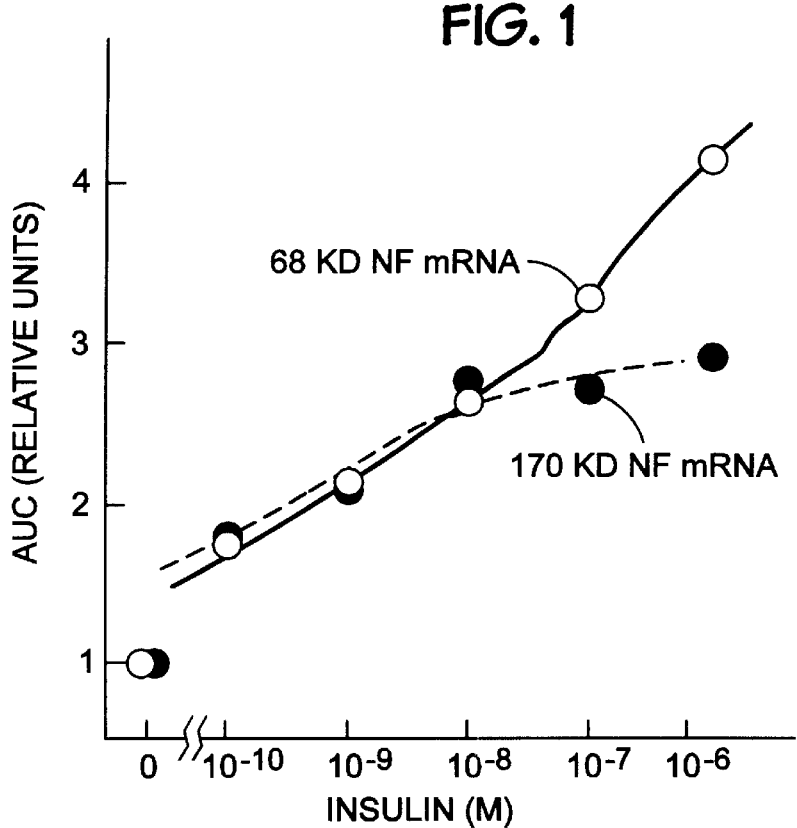

Altin, J.G. and R.A. Bradshaw. "Nerve Growth Factor and Related Substances: Structure and Mechanism of Action", pp. 129–180 in *Neurotrophic Factors*, Loughlin, S.E. and J.H. Fallon, eds. Academic Press, SAn Diego, CA. (1993).
Fallon, J.H, and S.E. Loughlin, "The Functional Implications of the Anatomical Localization of Neurotrophic Factors", pp. 1–24 in *Neurotrophic Factors*, Loughlin, S.E. and J.H. Fallon, eds. Academic Press, San Diego, CA. (1993).
Vernon, C.E., "Nerve Growth Factor and Epithelial Growth Factors", pp. 57–74 in *Homeostatic Regulators*, Wolstenholme, G.E.W. and J. Knight, eds. J. & A. Churchill Ltd. London. 1969.
Levi–Montalcini, R. and S. Cohen, "In vitro and In vivo Effects of a Nerve Growth–Stimulating Agent Isolated from Snake Venom", Proc. Nat. Acad. Sci. USA 42:695–699 (1956).
Levi–Montalcini, R., and S. Cohen, "Effects of the Extract of the Mouse Submaxillary Sqalivary Glands on the Sympathetic System of Mammals". Ann. N.Y. Acad. Sci. 85:324–341 (1960).
Bocchini, V. and P.U. Angeletti, "The Nerve Growth Factor: Purification as a 30,000–Molecular–Weight Protein", Proc. Natl. Acad. Sci. U.S.A. 64:787–794 (1969).
Angeletti, R.J., et al., "Subunit Structure and Amino Acid Composition of Mouse Submaxillary Gland Nerve Growth Factor". Biochem. 10:463–469 (1971).
Angeletti, R.H., et al., "Amino Acid Sequences of Mouse 2.5S Nerve Growth Factor. II. Isolation and Characterization of the Thermolytic and Peptic and the Complete Covalent Structure". Biochem. 12:100–115 (1973).
Angeletti, P.U., et al., "The Nerve Growth Factor (NGF): Chemical Properties and Metabolic Effects", Adv. Enzymol. Relat. Areas Mol. Biol. 31:51–75 (1968).
Bradshaw, R.A. et al., "Nerve Growth Factor and Insulin: Evidence of Similarities in Structure, Function, and Mechanism of Action", Rec. Progr. Horm. Res. 30:575–596 (1974).
Neurite Formation Modulated By Nerve Growth Factor, Insulin, and Tumor Promoter Receptors, Intern. J. Neuroscience 26:109–127 (1985).
Molecular Mechanisms of Neurite Formation Stimulated By Insulin–Like Factor and Nerve Growth Factor, Current Topics in Membranes & Transport 31:31–78 (1987).
Ishii et al., "Insulin, IGFs, and Their Receptors in the Central Nervous System"(Raizada et al. eds., Plenum Pub. Corp., 1987).
Recio–Pinto et al., Brain Research 302:323–334 (1984).
Recio–Pinto et al., The Journal of Neuroscience 6(5):1211–1219 (1986).
Fellows et al., Soc. Neuroscience Abstr. 13:1615 (Abstr. 445.14) (1987).
Hansson et al., Acta Physiol. Scand. 126:609–614 (1986).
Ishii et al., Int. J. of Neuroscience 26:109–127 (1985).
Ishii, Curr. Topics in Membrane & Transport 31:31–78 (1987).
Snyder et al., Brain Res. 565–571 (1980).
Kandel et al., "Principles of Neural Science," Elsevier Science Publishing Co., Inc., New York, pp. 250–251 (1991).
Mill et al., Proc. Nat'l Acad. Sci. 82:7126–7130 (1985).
Varon et al., Dev. Neurosci. 6:73–100 (1984).
Fingl et al., "The Pharmacological Basis of Therapeutics" (Goodman et al. eds.), MacMillan Publishing Co., Inc., New York, pp. 1–45 (1975).

Felten et al., The Anatomical Record 206:49–59 (1983).
Sidenius et al., Diabetes 29:182–186 (1980).
Schmidt et al., Diabetes 32:532–540 (1983).
Sharma et al., Diabetes 26:689–692 (1977).
Kawamura et al., J. Neuropathol. Exp. Neurol. 40(b):658–666 (1981).
Clemmons et al., J. Clin. Endocrin. Metab. 75(1):234–238 (1992).
Frank et al., Diabetes 34:728–733 (1985).
Frank et al., Diabetes 35:654–661 (1986).
Giacca et al., Diabetes 39:340–347 (1990).
Guler et al., Acta Endocrinologica 121:456–464 (1989).
Hyer et al., Horm. Metabol. Res. 21:18–22 (1988).
Kandel et al., "Principles of Neural Science," Appleton & Lange, Norwalk, Conn., pp. 246–257.
Wallum et al., J. Clin. Endocrinol. Metab. 64:190–194 (1987).
Caroni et al., J. Cell Biol. 110:1307–1317 (1990).
Kanje et al., Brain Res. 486:396–398 (1989).
Yan et al., Neuron 1:335–343 (1988).
Sendtree et al., Nature 358:502–504 (1992).
Barinaga, Science 264:772–774 (1994).
Pardridge, Trends in Biotech. 12:239–245 (1994).
Gregoriadis et al., Trends in Biotech. 11:440–447 (1993).
Saneto et al., "Neurochemistry A Practical Approach," IRL Press, Oxford, pp. 30–45.
Sara et al., Progr. Brain Res. 73:87–97 (1988).
Alberts et al., "Molecular Biology of the Cell," Garland Publishing, Inc., New York, pp. 563 and 1070–1075 (1983).
Stedman's Medical Dictionary, Williams & Wilkens, Baltimore, pp. 270, 1047 and 1045 (1990).
Guler et al., Acta Endocrinologica 121:753–758 (1989).
Greene et al., J. Clin. Invest. 55:1326–1336 (1975).
Jakobsen, J. Neurol. Neurosurg. Psych. 42:509–518 (1979).
Mayer et al., Diabetologia 25:433–438 (1983).
Davies, "Timing and Site of Nerve Growth Factor Synthesis in Developing Skin in Relation to Innervation and Expression of the Receptor," Nature 326:353–358.
Roberts, Molecular and Cellular Biology of Insulin–Like Growth Factors and Their Receptors 107–116 (LeRoith & Raizada eds., Plenum Press 1989).
Raivich, "The Expression of Growth Factor Receptprs During Nerve Regeneration," Restorative Neurology and Neuroscience I 217–223 (1990).
Frank et al., "Binding and Internalization of Insulin and Insulin–Like Growth Factors by Isolated Brain Microvessels," Diabetes 35:654–661 (1986).
Ishii et al., "Insulin–Like Growth Factors Protect Against Diabetic Neuropathy: Effects on Sensory Nerve Regeneration in Rats," Journal of Neuroscience Research 40:138–144 (1995).
Wuarin et al., "Early Reduction in Insulin–Like Growth Factor Gene Expression in Diabetic Nerve," Experimental Neurology 130:106–114 (1994).
"Colorado State Researcher ID's Cause of Major Diabetes Complications; Breakthrough is Hoped to Lead to New Research into Treatment Avenues," Colorado State University NEWS (1995).
McIntosh et al., "Efficacy of Insulin–Like Growth Factor (IGF–1) in the Treatment of Behavioral and Cognitive Deficits Following Experimental Brain Injury," Soc. Neurosci. Abs. 20:192 (1994).

Reinhardt et al., "Insulin–Like Growth Factors Cross the Blood–Brain Barrier," Endocrinology 135:1753–1761 (1994).

Ishii, "Implication of Insulin–Like Growth Factors in the Pathogenesis of Diabetic Neuropathy," Brain Research Reviews 20:47–67 (1995).

Orr, "Biotech Companies Pursue Neurotrophins as Potential Neurodisorder Treatments," Genetic Engineering News 15:1, 12 (1995).

Prevette et al., "Insulin–Like Growth Factors Prevent the Programmed Cell Death of Developing Chick Spinal Motoneurons in Vivo," The New York Academy of Sciences, Abstract No. PII–10 (1992).

Gluckman et al., "A Role for IGF–1 in the Rescue of CNS Neurons Following Hypoxic–Ischmemic Injury," Biochemical and Biophysical Research Communications 182:593–599 (1992).

Poduslo, *Peripheral Neuropathy* (3d ed., Dyck et al. eds.) W. B. Saunders Co., Philadelphia, PA (1993) p. 282.

Jakowski, A., *British Journal of Neurosurgery* 9:303–317 (1995).

Saatman et al., "Insulin–Like Growth Factor–1 (IGF–1) Improves Both Neurological Motor and Cognitive Outcome Following Experimental Brain Injury," *Exptl. Neurol.* 147:418–427 (1997).

Fernandez et al., "Insulin–Like Growth Factor I Restores Motor Coordination in a Rat Model of Cerebellar Ataxia," *Proc. Natl. Acad. Sci. USA* 95:1253–1258 (1998).

Hatton et al., "Intravenous Insulin–Like Growth Factor–I (IGF–1) in Moderate–to–Severe Head Injury: a Phase II Safety and Efficacy Trial," *J. Neurosurg.* 86:779–786 (1997).

Baker, "Pharmacological Treatment of Traumatic Brain Injury: Following the Footsteps of Stroke," *Drug & Market Development* 9:60–64 (1998).

Loddick et al., "Displacement of Insulin–Like Growth Factors from Their Binding as a Potential Treatment for Stroke," *Proc. Natl. Acad. Sci. USA* 95:1894–1898 (1998).

Schmidt et al., *Diabetes* 34: 1230–40 (1985).

Schmidt et al., *Brain Res.* 387:325–36 (1986) (abstract).

Kasayama and Oka, *Am. J. Physiol.* 257:E400–404 (1989).

Faradji et al., *Actas Neurological Scandinavica* 81:402–406 (1990).

Hellweg et al., *J. Neurosci. Res.* 26:258–67 (1990).

Chakrabarti et al., *Brain Research* 523:11–15 (1990) (abstract).

Hellweg et al., *Neuroscience Letters* 125:1–4 (1991) (abstract).

Apfel et al., *Annals Neurology* 40:954 (1996).

Hellweg, et al., "Diabetes mellitus–associated decrease in nerve growth factor levels is reversed by allogeneic pancreatic islet transplantation," *Neuroscience Letters*, 125 (1991) 1–4.

S. Chakrabarti, et al., "Nerve growth factor (NGF), proNGF and NGF receptor–like immunoreactivity in BB rat retina," *Brain Research*, 523 (1990) 11–15.

Schmidt, et al., "Retrograde Axonal Transport of [$^{125}$I] Nerve Growth Factor in Ileal Mesenteric Nerves in Vitro: Effect of Streptozotocin Diabetes," *Brain Research*, 378 (1986) 325–336.

Johannes Jakobsen, et al., Retrograde Axonal Transport of Transmitter Enzymes, Fucose–Labeled Protein, and Nerve Growth Factor in Streptozotocin–Diabetic Rats, *Diabetes*, vol. 30, (Oct. 1981) 797–803.

S. Kumar, et al., "The Adminnistration of the Nerve Growth Factor to Children with Widespread Neuroblastoma," *J. of Pediatric Surgery*, vol. 5, No. 1 (Feb. 1970) 18–22.

* cited by examiner

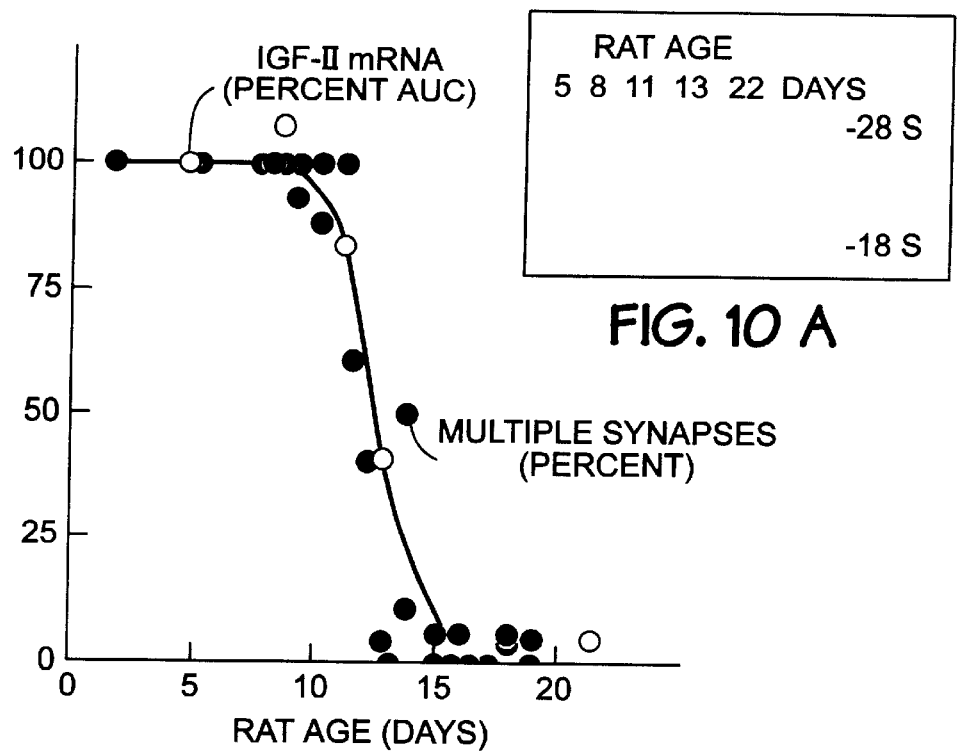
FIG. 10 A
FIG. 10 B
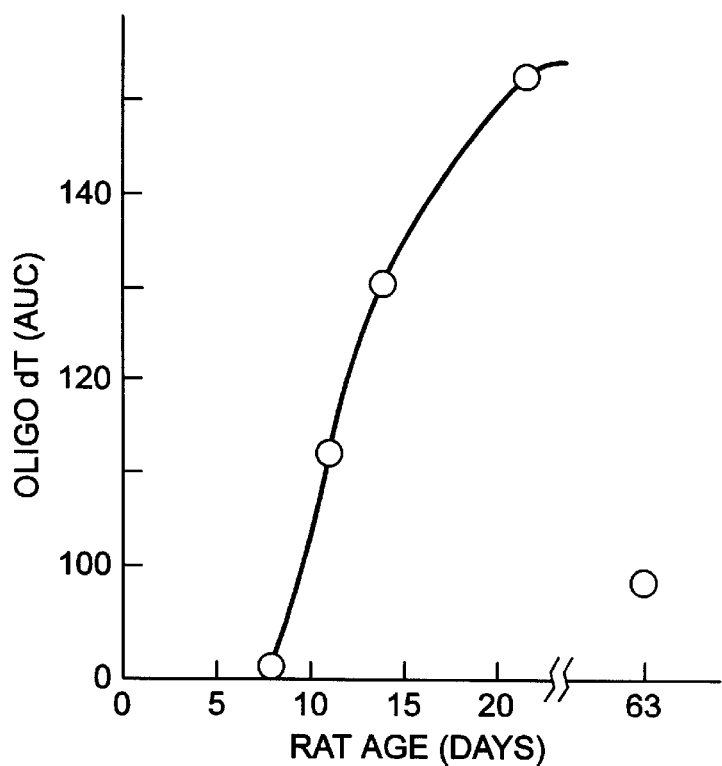
FIG. 10 C

METHOD FOR TREATING DIABETIC NEUROPATHY WITH NGF

RELATED MATTERS

This patent application is a continuation of co-pending application Ser. No. 8/398,852 filed Mar. 6, 1995, which is a continuation of application Ser. No. 07/909,200filed Jul. 6, 1992 (now abandoned), which is a continuation-in-part of application Ser. No. 07/781,908 filed Oct. 24, 1991 (now abandoned), which is a continuation-in-part of application Ser. No. 07/280,557 filed Dec. 6, 1988 (now abandoned).

FIELD OF THE INVENTION

This invention generally relates to therapeutic processes and compositions for ameliorating damage to mammalian nerve cells, as well as for healing and/or repairing said nerve cells, especially in the case of neuropathy. In this context, the term "nerve cells" should be taken to include neurons and neuroglia, whether in the central or peripheral nervous system, including the pre- and post- synapaptic elements of synapses and neuromuscular junctions. Similarly, the term "repair" should be taken to include recruitment of new nerve cells as well as restoration of function of existing nerve cells. Similarly, the expression "functionally repairing" nerve cells should include the concepts of recruitment of new nerve cells as well as the restoration function of existing nerve cells. This invention is particularly concerned with processes and compositions wherein insulin and insulin-like growth factors play a significant therapeutic role in neuropathy, especially diabetic neuropathy.

BACKGROUND OF THE INVENTION

The biochemistry and physiology associated with amelioration of damage to nerve cells, and induced reparations to nerve cells (including nerve cell elements such as neurites, synapses, epineurium, and endoneurium) have been the subject of many years of investigation. The field is complex and is often characterized by the presence of many subtle—yet extremely significant—distinctions. Some of these distinctions are, in turn, very much influenced by the underlying theories and/or assumptions employed by any given worker in this field. For example, much of the reported work has been done in conjunction with studies of particular kinds of damage to nerve cells through physical trauma or pathological disorders such as diabetic neuropathy. Those skilled in this art will appreciate that the processes of repair are not necessarily the same in the case of trauma as in pathological disorders. A great deal has been learned and some useful therapies have been implemented. A review of some of this past work will be helpful in establishing the scope of the herein described processes for healing nerve cells.

To these ends, it first should be noted that it has long been established that diabetic autonomic neuropathy includes abnormal regulation of blood pressure, bowel function, sweating, and skin temperature. Sensory neuropathy is known to include the absence of deep reflexes and loss of ability to perceive stimuli such as pain and temperature. Moreover, various stages of degeneration in sympathetic ganglion cells have been observed in the presence of this disease state. It is also known that conduction velocity is often reduced in sensory, motor and probably sympathetic nerves. Moreover, the prior art has, to some degree, appreciated that such reduction is partially preventable by insulin treatment.

It also has long been established that axon loss and segmented demyelination may be present in peripheral and sympathetic nerves. While demyelination suggests an indirect effect due to alteration in Schwann cell activity, the decrease in conduction velocity in juvenile onset and experimental diabetes is, however, not necessarily accompanied by morphologic alterations of the myelin sheath. Indeed, axonal disease is also known to be present in unmyelinated fibers. Moreover, while distal symmetrical polyneuropathy is more commonly encountered than symmetrical proximal motor neuropathy, or focal and multifocal neuropathies, the various forms of neuropathy can be present together in the same patient. Therefore, classifications into these subtypes is clinically useful, but may not truly reflect distinct categories of neuropathies.

It should also be noted that, when viewed in total, the prior art has shown that insulin and their receptors are present in the central nervous system, but the prior art has not shown whether or not the receptors can actually regulate neurite formation in vivo. For example, applicant's hereinafter cited past studies with respect to the effects of insulin and IGFs were conducted in vitro. Indeed, many technical considerations and references have indicated that in vitro studies do not reveal whether insulin, IGF-I, or IGF-II are active on the nervous system in vivo. For example, cells placed in culture are in fact removed from their normal in vivo environment. In such cases, they are removed from a host of supportive factors. Moreover, the capacity of cells to respond to an exogenous factor in vitro does not necessarily imply that that particular factor would have significant activity in vivo, or that a similar physiological role is played in vivo. For example, with respect to the latter, it is known that neurite outgrowth can be induced in vivo by actinomycin D or bromodeoxyuridine. One may not, however, infer that these compounds are physiological regulators of neurite outgrowth. Cultured cells are also removed from in vivo inhibitory substances. Such factors have been found to be present on CNS oligodendrocytes, which might help explain why regeneration is so poor in the CNS (Schwab and Caroni, 1988, J. Neurosci. 8:2381–2393). Hence, it is important to understand the teachings of this patent disclosure to appreciate and demonstrate the effects of insulin and IGFs on nerve cells in vivo. This is important because such a showing makes a distinction between the teachings of this patent disclosure and those made in various prior art references such as the Hansson et al, Acta Physiol Scand. 126 (609–614) (1986) reference. More will be said about the teachings of the patent disclosure vis-a-vis the scope of the teachings of this 1986 Hansson reference, especially in view of a subsequent Hansson paper published in 1987.

Those skilled in this art also will appreciate that previous theories regarding neuropathy include the involvement of small vessel angiopathy, secondary response to disturbances in Schwann call function, excess production and accumulation of polyols through the sorbitol pathway, alteration in lipid metabolism, decreased myoinositol production, and abnormal glycosylation of proteins. Detailed discussions of these theories are available throughout the literature (see for example (1) Thomas and Eliasson, In "Peripheral Neuropathy", Dyck et al., eds. WB Saunders Co., Philadelphia, 1984 pp 1773–1810 and (2) Brown and Greene, In "Peripheral nerve disorders, a practical approach" Asbury and Gilliatt, eds., Buttersworth, London, 1984 pp 126–53); but there is by no means any consensus as to the pathogenesis or extent of pathology (see Powell, Lab Invest 49:515, 1983).

In any event, none of the various prior art theories have thus far fully considered that insulin may act directly on neurons, or that IGFs, protein kinase C, and various neurotrophic factors such as nerve growth factor (NGF) may also play roles in the pathogenesis of such disorders. Moreover, in those instances where insulin was considered, no clear conclusions could be drawn. For example, Applicant and his coworkers previously have shown that physiological concentrations of insulin can reversibly increase the proportion of cells with neurites, as well as average neurite length, in cloned human neuroblastoma SH-SY5Y cells in culture (see, Recio-Pinto and Ishii, Brain Res 302:323–334, 1984). Other workers have established that this response can be inhibited by anti-insulin antiserum, and that it is correlated with occupancy of high affinity insulin receptors. It also has been established that insulin can directly enhance neurite formation and support neuron survival in primary cultures of sensory and sympathetic cells (see, Recio-Pinto et al., J Neurosci 6:1211–1219, 1986). The presence of other serum factors, or non-neuronal cells, did not appear to be required for the response.

These past speculations, based on in vitro studies, that insulin plays a role in the development and maintenance of the peripheral and central nervous system also found some support in past observations showing that insulin induces the precocious maturation of evocable synaptic transmission in culture. It was also noted that insulin could induce neurite growth, but such results were only shown with supraphysiological concentrations; hence it was not clearly established that insulin could act directly on neurons. Thus, the significance of these past in vitro observations could not be unambiguously interpreted at that point in time. The reasons for this inability are discussed in: (1) the previously noted Recio-Pinto and Ishii (1984) reference, (2) the Recio-Pinto et al. (1986) reference and (3) the Ishii et al. Int J Neurosci 26:109–127, (1985) reference which are each incorporated by reference into this patent disclosure. Considering the various limitations on these findings, it would be fair to say that it was not then known whether or not insulin had direct effects on the nervous system and hence, whether it might be useful to effect its repair.

It is also well known that insulin receptors and immunoreactive insulin are found in mammalian brain tissue. However, an understanding of the function of these receptors has proven to be rather elusive. Recent developments in procedures to culture central neurons are however finally beginning to yield important new insights. For example it is now believed that insulin has a number of effects on the specialized functions of neurons including the capacity to modify the firing frequency, increase neurotransmitter biosynthesis, and modify both transmitter uptake and release. It is also known that insulin receptors in brain have higher affinity, and are smaller due to decreased glycosylation, than those in peripheral tissues. The receptors on glial cells also are known to be similar to the peripheral type. The structural differences found in brain insulin receptors allude to a specialized role in neurons. It should be noted that many workers have questioned whether insulin could maintain or modulate neuron activity because it also has been established that there is fluctuation in its concentration between meals.

Applicant and his fellow workers have further sought to establish in vitro whether or not IGF-I and IGF-II (members of the insulin gene family sometimes referred to as somatomedins) also can induce neurite outgrowth and support the survival of sensory, sympathetic, and SH-SY5Y cells (see generally Recio-Pinto and Ishii, 1984; Recio-Pinto et al., 1986; Ishii and Recio-Pinto, "Insulin, IGF, and Their Receptors in the Central Nervous System", Raizada et al., eds., Plenum Pub Corp, New York, N.Y. pp 315–348, 1987), in a manner correlated with occupancy of IGF receptors (Recio-Pinto et al., 1986 reference).

Furthermore, Applicant's laboratory has previously demonstrated that physiologically meaningful concentrations of insulin in combination with insulin-like growth factor-I (IGF-I) or insulin-like growth factor-II (IGF-II) may act on neurons to induce neurite (axon and/or dendrite) growth in vitro (again, see the above noted Recio-Pinto and Ishii, 1984; Ishii et al., 1985 and Recio-Pinto et al., 1986 references). It should also be noted that IGF receptors and immunoreactive IGFs are also known to be present in brain. Nevertheless, the presence of insulin and insulin receptors, or IGFs and IGF receptors, in brain, as well as any activity of insulin or IGFs in vitro, provide no prior art as to the function of insulin or IGFs in nerve cells in vivo.

The mechanism by which these factors may stimulate neurite formation has been studied from several aspects, including by examining the expression of genes coding for major cytoskeletal proteins of axons and dendrites. It is now known that microtubules, comprises of alpha- and beta-tubulin heterodimers are essential structural elements of neurites. Moreover, microtubules are also known to be a part of the axonal transport apparatus.

It also was previously knows that NGF could increase the abundance of tubulin and microtubules in neurons; but it was not previously known whether the increase in tubulin could be due to an increased abundance of tubulin mRNA.

Applicant's laboratory also had established that tubulin mRNA becomes increased in response to NGF (see Fernyhough and Ishii, Neurochem Res 12:891–899, 1987). It also was established by other workers that insulin and IGFs can similarly increase the abundance of tubulin mRNAs as a prelude to neurite formation in vitro (see, generally, Mill et al., Proc Natl Acad Sci USA 82:7126–7130, 1985 which generally shows that insulin and IGF-II can induce neurites by increasing the abundance of tubulin mRNAs). Furthermore, these mRNAs are known to code for tubulin proteins which can assembly into microtubules.

Neurofilament proteins are also known to be important structural elements of neurites. For example, the 68 kD, 170 kD, and 200 kD neurofilament proteins can assemble to form neurofilaments. Similarly, NGF can increase the relative abundance of neurofilament mRNAs and proteins. Neurofilament gene expression appears to specify axonal caliber, and axonal caliber is one of the important determinants of conduction velocity. It also had previously been established by other workers that NGF can increase the levels of neurofilament proteins, and the abundance of 68 kD and 170 kD neurofilament mRNAs (see, for example, Lindenbaum et al., J Biol Chem, 263:5662, 1988). Neurofilament protein phosphorylation is also known to be modified.

As part of the work leading to this invention, the importance of phosphorylation in the shared mechanism also has been studied in Applicant's laboratory. While following this line of research, it was found that insulin, IGFs and NGF can alter the phosphorylation of a number of protein substrates in vitro (see Ishii and Mill, Curr Topics Membranes and Transport 31:31–78, 1987). It has also been noted that the beta-subunits of the insulin and IGF type I receptors are tyrosine kinases.

While following another line of research it also was established that activators of protein kinase C (receptor for tumor-promoting phorbol esters) could increase neurite formation in vitro (see, generally, Spinelli et al., Cancer Res 42:5067–5073, 1982; and Spinelli and Ishii, Cancer Res 43:4119–4125, 1983) while enhancing survival of cultured neurons (see Ishii, Cancer Res 38:3886–3893, 1978). However, it was not then known whether protein kinase C could enhance neurite formation through separate pathways, or whether it was part of the pathway of NGF, insulin, and IGFs. However, it now has been established that protein kinase C is in the neurite growth pathway of NGF in pheochromocytoma PC12 cells (Hall et al., J Biol Chem 263:4460–4466, 1988) and that sphingosine is a competitive inhibitor of protein kinase C, and can reversibly inhibit NGF-directed neurite formation.

The prior art with respect to NGF does not reveal whether insulin or IGFs would be useful for the purposes of this invention. NGF is not a member of the insulin or IGF gene family. Early studies on amino acid sequence suggested NGF was similar to proinsulin. However, now that their genes have been sequenced, it is clear NGF is not structurally related to insulin or IGFs. Moreover, the three dimensional structures of NGF and insulin/IGFs are very different. NGF even at high concentrations does not cross occupy insulin or IGF receptors. Moreover, one may not invoke the classic neurotrophic theory developed around NGF to argue that insulin/IGFs have the same effects and mechanisms as NGF. The classic neurotrophic theory suggests that NGF is released from targets tissues to help guide the advancing axon to such targets during development. In a startling recent development, Davies et al 1987 (Nature 326:353–358) has found that NGF mRNA and protein are produced in target tissues after rather than before or during synaptogenesis in development. NGF therefore could not be the guidance factor for axons, or responsible for synaptogenesis. The neurotrophic theory has been severely challenged. Therefore, it was not obvious that insulin/IGFs played a role in guidance of axons and formation of synapses during development, by simple analogy with NGF. Moreover, one might predict as obvious on the basis of the neurotrophic theory that infusion of NGF would increase the regeneration distance of peripheral nerves. However, infusion of NGF does not increase regeneration in sciatic nerves (Kanje et al., 1989, Brain Res. 485:102–104). This might be due at least in part to the unexpected down regulation of NGF receptors and net decreased transport of NGF during regeneration (Raivitch et al., 1990, Restorative Neurol. Neurosci. 1:217–223). Therefore, one may not use the observation that NGF can increase neurite outgrowth in sensory neurons in vitro to predict that it can do so in vivo. It follows that one may not infer a priori from similarity of actions between NGF and insulin/IGFs in vitro, that insulin/IGFs are active in vivo, Furthermore, potentiation between NGF and insulin/IGFs has been observed only in vitro with a neuroblastoma cell, which is an abnormal cell. It is not obvious that combinations of NGF with insulin/IGFs will cause potentiation in any particular therapeutic instance in vivo because potentiation has been studied with an abnormal cell in vitro. Indeed, such in vitro studies do not predict in vivo responses, and NGF fails to increase regeneration distance upon infusion in vivo.

Prior art with insulin does not reveal whether combinations with IGFs would be active in vivo. For example, it is known that chronic infusion of insulin, resulting in hyperinsulinemia, can produce degenerative, neuropathic changes in rats (Mandelbaum et al., 1983, Brain Res. Bull. 10:377–384; Westfall et al., 1983, J. Neurol. Sci. 61:93–107). Therefore, its usefulness in combination with IGF-I, IGF-II, or neurotrophic factors is not obvious and may be dependent on the particular condition, site, dose, and method of treatment. The combination with IGFs is not obvious, particularly in the case of diabetes, because in diabetes there can be accumulation of inhibitors of IGFs (Phillips et al., 1979, Endocrinology 104:1518; Taylor et al., 1987, Endocrinology 121:1360). Also, one may not exclude, a priori, the possibility that receptors for IGFs, like for NGF, may be lost in diabetes or other neuropathy or neurodegenerative condition.

This patent disclosure also provides a basis for formulating a new theory to explain the pathogenesis of diabetic neuropathy. The correlation of neuropathy with age, sex, and height was not readily explained by most of the previously noted theories. However, these correlations are not unexpected in light of Applicant's new theory. For example, polyneuritis is most commonly observed in the older patient, but may occur at any age. Motor and autonomic neuropathies are both known to be age-dependent. Age-dependency suggests that secondary factors, in conjunction with diminished activity of insulin, are likely to play an important role. While diminished insulin activity may predispose to neuropathy, functional impairment may or may not emerge, depending on the complex interplay of variables on the activity of neurotrophic factors which may sustain transcription, translation, and post-translational events above a critical threshold in some patients. In the case of the juvenile type I diabetic, any residual insulin activity could be considered a variable providing continuing neurotrophic support. High levels of IGF-I and IGF-II might be crucial factors further bolstering the nervous system of the juvenile insulin-dependent diabetic. When diabetic control becomes poor, type I patients are known to show lowered IGF-I (somatomedin C) activity; this may be of consequence for the transient neuropathy often associated with acute episodes. Between episodes the IGF activity may remain closer to normal. However, the slow decline in overall neurotrophic factor activity with age may cause a greater predisposition towards neuropathy in older diabetics.

There is also a known inverse correlation between height and both motor nerve conduction and vibratory sensation. Moreover, a higher incidence of neuropathy is observed in males. Males are on average taller than females. Although one may not discount the well known role of sex steroids on the nervous system, the correlation with height may reflect the greater tendency of neurons with longer of larger diameter axons to sustain damage when neurotrophic activity becomes border line. In a threshold phenomena, the metabolic need would be more acute in larger diameter and/or longer axons. The modest impairment of conduction velocity in motor nerves appears consistent with a preferential loss of larger diameter motor axons. Moreover, the stocking-glove pattern of neuropathy indicates a dependence on nerve fiber length, the lowest stocking being associated with the short pain fibers and the highest stocking with long fibers for sense of position and touch. The dissimilar stocking heights for different types of nerve fibers may also result from the unequal activity of the various neurotrophic factors on particular neuronal populations.

It may appear paradoxical that neuropathy is, in the same breath, positively correlated with particularly short stature in childhood diabetes. One interpretation is that diabetes predisposes children to short stature. Alternatively, because constitutionally short children have lower levels of IGF-I, those juvenile diabetics with reduced IGF-I levels may be at greater risk for both neuropathy and short stature. A good body of evidence indicates stature is correlated with IGF levels during development. Careful examination tends to reveal that sensory, motor, and autonomic neuropathy will generally co-exist. This theory, however, can less readily explain certain phenomena such as focal and multifocal neuropathy. It may be that ischemia and compression damage is more likely against neurons weakened by diminished activity of neurotrophic factors. Whatever the explanation for these particular phenomena, diabetes appears to represent a constellation of disorders and no single theory may be expected to explicate all of the many and diverse signs and symptoms. The challenge to basic and clinical diabetologists is to first devise a generally acceptable theory, and hope to eventually understand the exceptions.

In any event, applicant's work now indicates that neurotrophic agents, such as nerve growth factor and the insulin-like factors, share significant effects and common mechanisms with insulin. This understanding has, in turn, led to a clearer understanding of those mechanisms specifically leading to diabetic neuropathy. Previous theories concerned with its pathogenesis were often formulated under the belief that insulin's effects on neurons are primarily indirect. Applicant's more recent observations showing that insulin can act directly on the afflicted populations of neurons are now accommodated in applicant's new theory that neuropathy may arise, at least in part, from a cascade initiated by the reduced direct activity of insulin on neurons. A second cascade also is suggested by applicant's finding. This theory stands in contrast to most previous theories on the pathogenesis of diabetic neuropathy which were based by and large on the belief that insulin's effects on the nervous system are mediated predominantly indirectly through its actions on non-nervous tissues.

The present state of knowledge in this area should also be viewed with respect to the present treatment possibilities. Following many forms of neuropathy it is frustrating to neurologists that very little can be done beyond diagnosis. Particularly in diabetic neuropathy there is no consensus as to causation, and no consensus as to the optimum treatment. Those who believe that glycemic control is important, and strive to obtain tight metabolic control with insulin, despite the observation that patients continue to die of microangiopathy and neuropathy generally gets worse with time. There are ongoing therapeutic trials with aldose reductase inhibitors, myo-inositol supplementation, vitamins, and gangliosides, but none of these forms of experimental treatment are widely accepted as therapeutic. Therefore, the treatment is aimed in a nonspecific way at ameliorating symptoms. Autonomic diarrhea is treated with tetracycline; gastroparesis is treated with attempts to increase gastric emptying or surgery; anticholinergic agents are used to prevent gustatory sweating; orthostatic hypotension is treated mechanically, with plasma fluid volume expanders, and vasoconstrictor drugs; impotence is treated with prosthesis; bladder dysfunction is treated with attempts to improve bladder emptying; diabetic foot is treated with attempts to block ulceration; neuropathic joint degeneration is treated by immobilization; diabetic pain is treated by glycemic control, and weight loss. These treatments are all considered unsatisfactory and suboptimal. Symptoms may progress and greatly reduce the quality of life in afflicted individuals. In the case of Alzheimer's Disease, motor neuron disease, hereditary neuropathies, and many other neuropathies, there is simply no known or accepted satisfactory treatment. Generally speaking then, there is currently no useful alternative accepted procedure for performing the function of the processes and therapeutic agents of this patent disclosure in order to limit or treat injury in neuropathy, particularly diabetic neuropathy.

SUMMARY OF THE INVENTION

Applicant's research with respect to the effects of insulin and IGFs on nerve cells has, among other things, led to a new hypothesis regarding the generalized mechanism for the induction and repair of nerve cells which have undergone functional damage. The testing of this hypothesis has, in turn, led to the herein described processes and therapeutic formulations which are useful for ameliorating damage to, healing, and repair of mammalian nerve cells. Such processes and formulations are also particularly well suited to prophylaxis with respect to nerve cells.

Concerning prophylaxis, certain neurodegenerative disorders such as senile dementia or Alzheimer's disease, are due to progressive loss of neurons. One possibility is that with age, or due to other causes, the activity of insulin, IGF-I, IGF-II neurotrophic factors, singly or in combination, may be diminished and support for neurons lost. The invention can be used to substitute for diminished activity, and if applied sufficiently early, continuous application may prevent or ameliorate the progression of the neurodegenerative disorder. In diabetic neuropathy there can be loss of nerve cells. If administered in a timely fashion IGFs may be prophylactic. Even in the case of acute trauma or exposure to neurotoxins, death of neurons is not necessarily immediate, and may follow as a result of reactive injury. Prompt intervention with this invention may be prophylactic for reactive injury as well as neuropathy.

Applicant has established that IGF-I and IGF-II can be efficacious independent of any combination with insulin and that combinations with protein kinase C activators, as well as with insulin, IGF-I and/or IGF-II, and various neurotrophic factors, can have additive effects on nerve cells. Applicant does not however discount the potential involvement of glia and Schwann cells, which express insulin, IGFs and neurotrophic factor receptors or discount the potential that neuroglia cells can respond to and/or produce neurotrophic factors which may help support peripheral and central neurons.

In any case, applicant's hypothesis, and the processes and therapeutic agents related to it, are especially concerned with neuropathy which arises from a diminished activity of insulin, IGFs and other neurotrophic factors. It should also be noted in passing that the expression "diminished activity" is to be taken in the broad sense. For example, as it applies to but is not limited to insulin, it might result from primary or secondary insulin insufficiency (decreased production of insulin or productions of less efficacious insulin molecules), decreased numbers, affinity, or efficacy of insulin receptors, and post-receptor alterations in the complex train of events leading to the response. It should also be noted here that oral hypoglycemic agents (e.g., sulfonyl ureas) are known to be active through their ability to stimulate insulin secretion or enhance insulin activity; hence for the purposes of this patent disclosure, use of the term "insulin" should be taken to include, but not be limited to, hypoglycemic agents as well as insulin itself. Such hypoglycemic agents would include sulfonylureas such as tolbutamide, acetohexamide, tolazamide, chlorpropamide, glyburide and glipizide used at dosages set forth as efficacious in publications such as the United States Phrmacopeia Dispensing Information, Physician's Desk Reference, and the like.

Applicant's research applicant now indicates that the syndrome of diabetic neuropathy has its source mainly in two cascades initiated by diminished insulin activity. Moreover, applicant now also believes that in the first cascade of his proposed mechanism, a loss of insulin activity might directly diminish the cellular content and/or activity of proteins necessary for the structure and function of nerve cells. Alternatively, or in an exacerbating mechanism of a second cascade, it is proposed that insulin activity, individual genetic make-up, and age-dependent variables may modulate the activity (again in the broad sense) of other neurotrophic factors such as the insulin-like growth factors (IGFs) and nerve growth factor (NGF). The severity and extent of neuropathy may ultimately be dependent on the combined activity of the various neurotrophic factors in individual diabetics. The consequences are however, made somewhat predictable on the basis of the spectrum of insulin and other neurotrophic factors' partially elucidated effects and mechanism in neurons.

In any event, it should now at least be recognized that all of the complexities associated with diabetic neuropathy may not be caused by a diminished direct activity of insulin on nerve cells. For example, some of the mechanisms identified in the previously noted metabolic theories may act to varying degrees in concert with the ones suggested here. Applicant's theory may also offer more useful explanations for many aspects of the clinical syndrome and for a significant body of observations in experimental diabetes. Moreover, this increased understanding of the physiology and mechanism of neurotrophic polypeptides now provides a new conceptual framework for formulating predications and designing new modalities of treatment such as those described in this patent disclosure.

Many of the processes and compositions of this patent disclosure also are based upon Applicant's findings that loss of activity of other neurotrophic factors, combined with the loss of insulin activity, may reduce the total trophic influence on nerve cells below a critical threshold. This circumstance now appears to be especially true in the case of diabetes. Hence it is postulated that the consequence for neuropathy may also be particularly predicted on the basis of the conjunctive insulin and insulin-like growth factor's actions and mechanisms in nerve cells. Moreover, applicant's theory now provides a much more complete explanation for many aspects of the complex syndrome seen in neuropathy. This in turn has led to the herein disclosed therapeutic processes and compositions for healing, regenerating and ameliorating damage to mammalian nerve cells. Applicant would also add that the results of preliminary tests in diabetic rats have now borne out several predications of this theory.

Applicant's theory also provides a reasonable explanation for many distinguishing features of neuropathy. For example, Applicant has found that a decrease in insulin activity, alone or together with a loss of activity of other neurotrophic factors, might trigger a cascade in which decreased levels of transcripts for tubulins, neurofilaments, and other structural proteins may contribute to the diminished axonal transport, axonal diameters, and numbers of axons observed in diabetes. This cascade includes the altered phosphorylation of proteins which regulate the function of neurons. Applicant believes that such a reduction in trophic factor activity might lead to the observed decreases in ganglion cell size and cell death. Significantly, the previously noted sympathectomy caused by an anti-NGF antiserum is believed to mimic that of the autonomic syndrome. The resultant immunosympathectomy includes reduced ganglia volume, loss of neurons, decreased content and capacity for uptake of catecholamine and loss of nerve terminals. Moreover, an important determinant of conduction velocity is axonal diameter, and diameter appears to be regulated by neurofilament content and give expression. Therefore, a reduction in the production and transport of neurofilament proteins might contribute to the reduced conduction velocity, at least in the late stages of diabetes. However, in the early stages of diabetes, conduction velocity is impaired at a time prior to any indications of change in axonal diameter, and it is uncertain whether there is any correlation between axonal diameter and the fundamental cause for decline in conduction velocity.

Neurotrophic factors also may act, in part, through protein kinase C. For example, applicant has Shown that activators of protein kinase C can mimic many of the effects of neurotrophic factors. Applicant has also shown that competitive inhibitors of such activators can inhibit neurite formation induced by insulin, IGFs, and NGF, as well as by protein kinase activators. Other contributing factors to consider might include the activity of ion channels, $Na^+/K^+$ ATPase, phosphorylation and/or other post-translational events under regulations by neurotrophic factors. These in vitro studies, however, do not predict with any certainty that activators of protein kinase C would be effective in vivo, particularly in the altered environment of diabetes.

However, those skilled in this art also will appreciate that, regardless of the assumptions regarding this theory, one may not know a priori whether IGFs are effective in neuropathy. For example, diabetes may involve metabolic toxicity to nerve cells, and it cannot be known a priori whether IGFs can protect against toxicity. Moreover, diabetic neuropathy is not presently generally appreciated or known to be the consequence of a fundamental defect in role of insulin, IGFs or neurotrophic factors on regeneration or neurite growth; even if IGFs were effective on regeneration, one could not know a priori whether IGFs would treat important symptoms of neuropathy. Even if it were known that neuropathy was the consequence of reduced IGF activity due to the presence of inhibitors of IGFs, it would not be known whether treatment with IGFs would be effective without specific test.

In any event, and regardless of the theoretical considerations with respect to the pathogenesis of various neuropathies, the herein disclosed family of processes and therapeutic compositions are effective in ameliorating damage to nerve cells, prophylaxis and healing and/or repairing functionally damaged nerve cells. Therefore such processes and therapeutic agents can form the basis of a chemotherapeutic regimen leading to prophylaxis and repair of neural systems suffering the consequences of trauma, of neuropathy in general, and diabetic neuropathy in particular. Applicant has also found that these effects also may be enhanced by the production of an environment containing protein kinase C activators and/or NGF. That is to say these effects were observed in conjunction with, but exceeded the normal scope of neurotrophic activity of nerve growth factor and activators of protein kinase C.

Such processes will generally comprise administering to said nerve cells a pharmaceutically acceptable composition comprised of any of the ingredients noted below in amounts effective in accelerating said prophylaxis, healing and/or repair. It should also be noted that these compositions can be used as a prophylaxis to healthy, as well as damaged, nerve cells.

Hence, the processes and compositions of this patent disclosure can employ any of the following therapeutic agents and combinations of therapeutic agents: (a) IGF-I, (b) IGF-II, (C) IGF-I and IGF-II, (d) insulin arid IGF-I, (e) insulin and IGF-II, (f) insulin, IGF-I and IGF-II, (g) neurotrophic factors including NGF, (h) neurotrophic factors and IGF-I, (i) neurotrophic factors and IGF-II, (j) neurotrophic factors arid insulin, (k) neurotrophic factors, IGF-I and IGF-II, (l) neurotrophic factors, insulin and IGF-I, (m) neurotrophic factors, insulin and IGF-II and (n) neurotrophic factors, insulin, IGF-I and IGF-II. The effects of insulin and/or IGFs are found to be additive and/or synergistic with the neurotrophic factor, NGF, and it takes no great leap in logic to assume that other neurotrophic factors may also produce additive or synergistic effects. Such neurotrophic factors may include, but are not limited to, nerve growth factor (NGF) and other members of the NGF gene family, epidermal growth factor, glial growth factor, basic and acidic fibroblast growth factor, platelet derived growth factor, brain derived neurotrophic factor, ciliary neurotrophic factor, leukemia inhibitory factor, neurotrophin NT-3, and the like. Moreover, the disclosed processes and therapeutic agents can be expanded to include the use of protein kinase C activator(s) in amounts effective in accelerating said healing and/or nerve repair. That is to say for example, that since applicant also has established that protein kinase C is in the neurite growth pathway for NGF, insulin, and IGFs in sympathetic neurons, such activators also can be added to the above compositions to produce some preferred forms of these therapeutic agents. Those skilled with this art also will appreciate that protein kinase C itself probably cannot be given as a drug because it would not permeate the cell. However protein kinase C activators can be used. Hence, the above therapeutic agents and combinations of therapeutic agents can also employ protein kinase C activators such as, for example, phorbol esters, teleocidin, mezerein, ingenol dibenzoate, diacyiglycerol and the like as part of their formulations.

Again, doses active in vitro for IGFs, generally 0.1–10 nM, do not disclose the doses which would be active in vivo. For example, in the intact vertebrate, consideration also must be given to factors not present in culture, such as IGF binding proteins, route of administration and potential first pass effects, biotransformation, blood-brain and blood-nerve barriers, preferential binding of IGF-I or IGF-II in particular body compartments such as the cerebrospinal fluid which has predominance of IGF-II binding components, and whether conditions of neuropathy such as diabetes or individual need may modify these variables. Neuropathy may alter the biochemical mileau in which IGFS must act. The presence of IGF binding proteins selective for one IGF in a particular body compartment may render that, but not the other IGF, essentially inert. There are at least five IGF binding protein subunits which form at least six IGF binding proteins that bind and inactivate IGF-I and IGF-II in various tissues (Hardouin et al, 1987, Eur. J. Biochem. 170: 121–132). The amounts of the particular binding proteins vary with development, metabolic state, and may vary with species. The type and amounts of binding proteins in the peripheral circulation are different from those in tissues such as cerebral spinal fluid. For example, in the latter, the predominant binding protein sequesters IGF-II with 40 times greater potency than IGF-I (Hossenlopp et al, 1986, FEBS Lett. 208: 439–444). If one desired to infuse IGFs into spinal cord, it is possible that the same dose of IGF-I may be much more efficacious than IGF-II because IGF-I would be sequestered to a much lesser degree. Therefore, it is not obvious from in vitro data that one may simply replace IGF-II for IGF-II, and the selection is likely to depend on the particular site targeted for therapy. Also, exogenous IGFs may need to cross various barriers to reach their therapeutic targets, and it is not known whether one IGF or the other has a selective advantage in crossing blood-brain, blood-nerve, or epineural barriers. For example the dose to treat focal neuropathy might be tiny if delivered locally, whereas the dose for treatment of polyneuropathy would be much larger. Moreover, unlike the in vitro situation, the ICP dose requirement would be variable depending on the individual, age, diet, level of activity, trauma, and other factors. Particularly in the case of diabetes, because the insulin requirement for an individual is variable, it is likely that the IGF requirement would also be variable.

Applicant also has shown that IGF-I mRNA content declines in diabetic rats (see below). Under clinical conditions, the endogenous and exogenous insulin levels would be variable, and IGF-I activity is also likely to be variable. It would not be possible to predict the replacement dosage from simple consideration of in vitro data. A dose of 1 nM (7 ng/ml) might be predicted as active in viva on the basis of in vitro data. However, this low a dose has not been found active by Applicant or Kanje et al (1989). The dose would need to be titrated to the requirements of an individual by methods known to this art and then modified with need.

It also should be noted that even though the previously noted in vitro established prior art do not render applicant's in viva utilities for the various compounds (or combinations or permutations thereof) "obvious" to those skilled in this art, applicant's work, as manifested in this patent disclosure, now enables one of ordinary skill in this art to determine the appropriate dosage/regimen for a wide variety of indications (disease and/or trauma) through routine trial work and experimentation. Nevertheless, applicant would point out that, in many cases, the herein disclosed processes will be most effective when the insulin component of a given therapeutic composition is administered at a concentration of from about 0.1 nM to about 10 nM, the IGF-I component is administered at a concentration of from about 20 nM to about 10 uM and the IGF-II is administered at a concentration of from about 20 nM to about 10 uM. When they are employed, a kinase C activator component should be administered in a concentration which generally will be from about 0.1 nM to about 10 uM. When it is employed, the neurotrophic factor concentration should be from about 0.01 nM to 1 uM. It should also be noted that all concentrations given in this patent disclosure are to be taken as serum concentrations unless it is specifically stated otherwise.

Such formulations may also include many pharmaceutically acceptable carriers as well as salts of the ingredients noted above. For example, those skilled in this art will appreciate that if the compounds of this invention are in the form of dry salts, they also may be associated with any number of pharmaceutically acceptable carriers well known to the art. Salts of sodium and of potassium would be common, but by no means limiting examples of pharmaceutically acceptable salts in which the compounds of this invention could be formulated. Formulations may also include acetate, protamine, zinc, or other substances intended to increase the duration of action or solubility state of IGFs. Furthermore, IGFs are those polypeptides which bind to and activate IGF receptors, and which contain significant sequence homology with IGFs (65% or greater), including IGFs from various species, variant forms of IGFs produced as a result of alternative splicing and/or alternative polyadenylation, biosynthetic IGFs, truncated IGFs, derivatives of IGFs, arid IGFs genetically engineered to enhance stability, permeability, efficacy, or otherwise improve the pharmacokinetic, pharmacodynamic, or pharmaceutical properties of IGFs. The invention also encompasses various modes of delivery of IGFs, including from pumps or other mechanical devices, slow release from encapsulation devices, and release from implanted tissues or cells which may produce IGFs either naturally or due to transfection. Procedures to increase synthesis of endogenous IGFs, decrease their elimination, or increase their stability for purpose of treatment of neuropathy, particularly diabetic neuropathy are additionally encompassed by this invention.

Applicant's findings also suggest a tentative model for how IGF-II in muscle might promote neurite growth and synaptogenesis, and be regulated by innervation, it has been noted that early in development the IGF-II gene is expressed in developing myotubules (although the possibility that other types of cells may be involved is not excludable at this time), predisposing towards neurite elongation and synapse formation. The abundant IGF-II transcripts may stimulate synapse formation with lack of discernment between uninnervated and innervated muscle fibers, leading to multiple innervation. The influence of synaptogenesis on maturation of muscle provides an as yet unidentified signal which feeds back to inhibit the accumulation of IGF-II mRNAs. Potential signals include a) the release of neurotransmitter or other substance from nerve terminals, b) the physical contact between nerve terminals and muscle basement membrane, and c) muscle contraction. As the stimulatory influence of IGF-II proteins begins to wane, multiple synapses are no longer supportable and superfluous ones are eliminated. The interruption of nerve impulses, through nerve transection, lifts the inhibition and IGF-II mRNAs again become more abundant. This, in turn may help stimulate nerve regrowth and the restoration of synapses.

The regrowth of axons to denervated muscle recapitulates many aspects of development. Intact adult muscles do not accept additional innervation, but denervated muscles, like embryonic muscles, are highly receptive to innervation. The up regulation of IGF-II mRNA abundance in denervated muscles may contribute to the repair of damaged nerves. In agreement with this hypothesis, gene expression became selectively elevated in denervated muscles, but remained low in intact calf muscles following transection of the sciatic nerve. Surgical stress was not the cause of the change in gene expression, because IGF-II transcript levels remained equally low in sham-operated and unoperated animals. Moreover, the IGF-II multi-transcripts were expressed in the same sizes and ratios in denervated and developing muscles. The results suggest that the abundance of IGF-II transcripts may be a critical determinant of the biochemical state in muscle receptive to the development or repair of innervation.

However, these studies with IGF-II gene expression are correlative only, and one may not know whether endogenous IGFs actually increase regeneration of nerves or synapses simply on the basis of increased IGF protein or mRNA in regenerating tissue. This reservation applies as well to the increased endogenous IGF-I protein observed by Hansson et al (1986) in regenerating nerves. For example, NGF protein and mRNA are increased in crushed sciatic nerve, but infused NGF does not increase regeneration rate. This observation shows, furthermore, that the capacity of NGF to increase nerve axon growth in vitro does not predict its activity in vivo. Whether infused NGF can potentiate response to IGFs in vivo remains to be established. GAP43 is increased in regenerating nerves, but GAP43 does not increase nerve regeneration. Tubulin is increased in regenerating nerves, but infusion of tubulin would not increase nerve regeneration. Therefore, in general, the observation that a protein is increased during regeneration does not predict whether that protein can increase regeneration. One may not exclude the possibility that increased IGFs during regeneration may serve altogether different functions, such as to signal macrophages to enter the crushed nerve to clean up debris.

Moreover, it would be even more difficult to predict whether exogenous IGFs would increase repair or regeneration of the nervous system. One must contend with the blood-brain and blood-nerve barrier. The special capillaries have tight junctions and lipophilic small drugs can enter the brain by passive diffusion. However, ionic or polar compounds cannot cross the blood-brain barrier, and very large molecules such as proteins are known to be excluded. Undoubtedly, the blood-brain barrier protects the brain from the surges in insulin concentrations following meals, and from immunoglobulins in the circulation. Less than 0.1% of immunoglobulins or serum albumin can cross the blood-brain barrier. There would be a discontinuity in the blood-nerve barrier at the site of nerve crush, and exogenous IGFs might be transiently active until the blood-nerve barrier were repaired. However, this assumes that exogenous IGFs acting only at a limited region near the growing tips of axons would be sufficient to improve regeneration. Exogenous IGFs infused near nerve would need to contend also with the epineurium, a thick sheath surrounding nerves and generally considered impenetrable to large proteins. Again in the special case of crush, there would be discontinuity in the epineurium, but it would still be uncertain whether exogenous IGFs acting at the limited site of crush would be efficacious on axons. Exogenous IGFs would encounter IGF binding proteins in the circulation and in the extracellular fluid, and may well never reach the limited site of entry. Thus, there is no way of knowing, a priori, whether exogenous IGFs would be active on regeneration.

Secondly, in the case of neuropathy, particularly diabetic neuropathy, the biochemical mileau is abnormal, and one may not know a priori whether exogenous IGFs would be efficacious in prophylaxis, repair or regeneration. For example, in type II diabetes, circulating insulin concentrations are often normal or even elevated, but there is a tissue resistance to insulin. There is also tissue resistance to IGFs in diabetes. For example, antibodies to IGF receptors and inhibitors of IGFs have been described to be present in diabetic serum. In the case of motor neuron disease (amyotrophic lateral sclerosis) there is a progressive loss of motor neurons in the spinal cord and neurons of the motor nuclei of the lower brain stem, yet the many other types of nerve cells are spared. The pathogenesis is unknown, but it is known that serum from such patients contain some substance or substances that is toxic to motor neurons. In this altered biochemical mileau, clearly the endogenous neurotrophic factors are incapable of supporting the motor neurons. A priori there is no basis for knowing whether exogenous IGFs would support motor neurons against circulating toxic factors. In the case of human neuroblastoma, our in vitro studies with human SH-SY5Y and other neuroblastoma cell lines show that IGFs are mitogenic agents. Thus exogenous IGFs may well exacerbate this form of neuropathy, and cause a more rapid growth of this cancer. For these reasons, and because of the blood-nerve and epineural barrier, as well as IGF binding proteins, one could not predict a priori with any confidence from our studies or that of Hansson et al (1986) that exogenous IGFs would be efficacious in neuropathy, particularly diabetic neuropathy.

in order to adequately deal with one of the subtleties of the teachings of this patent disclosure, it also is necessary to carefully assess what inferences may reasonably be drawn from the teachings of Hansson et al (1986) Acta Physiol. Scand. 126: 609–614. First, it should be noted that these workers transected the sciatic nerve, inserted the two ends of the nerve into a silicon tube, which bridged a 10 mm gap between the ends of the transected nerve. They then observed that IGF-I was high in the proximal nerve stump and in the gap, but not in the distal nerve. Based on these observations, they stated "The finding of increased IGF-I activity in regenerating peripheral nerves and that IGF-I may play a key role in regeneration is supported by the report that proinsulin, insulin and IGF-II, peptides with high structural homology to IGF-I, promote neurite outgrowth from neuroblastoma cells (Recio-Pinto & Ishii, 1984)." However, this statement of Hansson et al (1986) was cautiously couched in terms of unsubstantiated assumptions; and indeed it was, in effect, abandoned in a subsequent publication hereinafter noted. That is to say that the increased IGF-I in Schwann cells may not be produced in Schwann cells, but might be released from the transected nerve and become sequestered by Schwann cells. It was discussed above that the in vitro study of Redo-Pinto & Ishii (1984) cannot teach whether IGFs would support regeneration in vivo. It was discussed above that an increase in IGF-I in the nerve of itself cannot teach whether IGF-I supports regeneration. For example, NGF is increased in lesion nerves, but infused NGF has no effect on regeneration in crushed nerves (Kanje et al., 1989), and worse, can cause increased death of motorneurons (Miyata et al., 1986, J. Neurosci. 6: 2012–2018). That is to say that those skilled in the art will also appreciate that nerve transection is not a generally accepted model for regeneration. This follows from the fact that nerves are extremely poor at growing across gaps, and the few of the many hundreds of axons which may grow across gaps will generally regenerate aberrantly to incorrect sites. Therefore the statement of Hansson et al (1986) about "regeneration" is based on a model where regeneration does not occur. Thus, a correlation cannot be made between their increased IGF-I and "regeneration". Therefore, the usage of the term "regeneration" by Hansson et al (1986) is more in the nature of an operational definition based on the limited sprouting of axons in a transected nerve, and quote marks around the term will hereafter be used to distinguish Hanssori's usage of the term. For example, this is not the normal usage of the term as recognized in Dorland's Illustrated Medical Dictionary, which defines regeneration as "The natural renewal of a substance, such as a lost tissue or part." Natural renewal generally does not occur after nerve transection. This all goes to say that in considering this term in evaluating such statements, it also is necessary to closely examine the use of the term in relationship to the environment in which it is used.

Hansson et al (1987) Cell Tissue Res. 247: 241–247, in effect, recognized this and turned their attention to nerve crush, which is a widely accepted model for successful regeneration. Here the axons enter the basal lamina tubes below the site of crush to be guided back towards their original targets. The continuity of the basal lamina tubes are not lost in crush, and axons do not become misguided or lost as in transection. The neurotrophic theory (Mobley et al, 1977, New Eng. J. Med. 297: 1096–1104, 1149–1158), which is the basis for their interpretations, teaches that neurotrophic factors are released from target cells, picked up by the ends of axons, and transported in a retrograde fashion in axons back to the neuron cell body to stimulate growth and regeneration. Thus, one might expect that following crush, IGF-I would accumulate below the site of crush as NGF is known to do. In contrast, what Hansson et al (1987) observed was that IGF-I accumulated mostly above the site of crush. They therefore reasoned that IGF-I was synthesized in the nerve cell, rather than the target cells, and was transported distally, down the axon to accumulate above the site of crush, just as tubulin, neurofilament, actin, neurotransmitters and peptides, which are other substances produced in neurons. A smaller amount of IGF-I accumulates below the crush because the IGF-I reaching the axon terminals become degraded, and only a few remaining IGF-I molecules can return by retrograde transport. Their earlier observation that Schwann cells are positive for IGF-I following transection could be explained by release of IGF-I from axons and subsequent binding to Schwann cells. Thus, Hansson et al (1987) appears to have, in effect, abandoned their earlier model that IGF-I supports "regeneration" as a neurotrophic factor by virtue of the fact that no mention is made of what was just a few months earlier considered as a "key role in reqeneration". Consequently, the Hansson et al (1986) studies cannot be said to teach whether IGF-I plays a role in regeneration. Moreover, Hansson et al did not study effects of insulin, IGF-II or their combinations with IGF-I. As a result, Hansson et al gave no clear cut implications concerning applicant's findings with respect to insulin and IGF-II, or their combinations with or without IGF-I.

Nevertheless, the previously noted statement by Hansson et al (1986), must be placed in the overall context in which applicant's invention resides. This can be done by noting that Hansson's model of "regeneration" is based on the limited capacity of axons to sprout for a few mm from the end of a transected nerve into a gap. Therefore, their "regeneration" has no practical utility. Their "regeneration" is not equivalent to "repair" (again the term "repair" can be taken to include "functional repair") following crush, where axons can grow back to their targets, form synapses, and become functional. Again, when Hansson et al (1987) later studied crush and functional repair, they in effect abandoned their earlier statement concerned with a role for IGF-I in "regeneration". Hence, it cart be said that Hansson et al (1986) does not reasonably teach that their limited "regeneration" is the equivalent of functionally repairing, which is the subject matter of this aspect of the invention.

Furthermore, the "regeneration" observed by Hansson et al (1986) should not be considered as conclusive prior art with respect to neuropathy, particularly diabetic neuropathy. That is to say that the field of nerve regeneration (medical dictionary usage here) is distinct and separate from that of neuropathies, particularly diabetic neuropathy. The field of nerve regeneration is predominantly concerned with the particular problem faced with injury to nerves usually following trauma. A representative example of the concerns of nerve regeneration is provided by the book "The Current Status of Peripheral Nerve Regeneration" (T. Gordon et al., eds.), Alan R. Liss, Inc., New York, 1988. The objective stated in the preface was "to bring together scientists from many different disciplines to focus their attention on the specific problem of peripheral nerve regeneration," and the book contained the published contributions of these scientists as presented to hundreds of scientists who attended this symposium. Out of 48 contributed papers and posters, virtually all were concerned with regeneration following trauma. Not a single study was concerned with neuropathies encompassed by this invention such as diabetic neuropathy, motor neuron disease, Alzheimner's Disease, metabolic neuropathy, diseases of cranial nerves, diseases of spinal roots, neuropathy due to peripheral vascular diseases, inherited neuronal atrophy and degeneration, Refsum Disease, porphyric neuropathy, alcoholic neuropathy, uremic neuropathy, hepatic neuropathy, amyloid neuropathy, sarcoid neuropathy, neuropathy due to infection, toxic neuropathy, neuropathies associated with proteinemias, metal neuropathy, neuropathy associated with neoplasms, post-polio syndrome, neuropathy secondary to chemotherapy, or the like. Other symposia and books show a similar dichotomy between regeneration and neuropathy. These are generally considered separate and distinct fields.

A major reason for this dichotomy, is that it is not historically or generally considered that the studies on regeneration have a direct bearing on the treatment of neuropathy, particularly diabetic neuropathy. For example, in uremic neuropathy there is chronic kidney failure, and a buildup of toxic substances in the blood, predisposing to neuropathy. In amyloidosis there is extracellular deposition of a fibrillar protein, or amyloid, in various tissues, predisposing to neuropathy. There is no consensus for a relationship of these neuropathies, particularly diabetic neuropathy to regeneration. Therefore, the relationship to "regeneration" as suggested by Hansson et al (1986) would not force one skilled in the art to any meaningful conclusions regarding neuropathy, particularly diabetic neuropathy.

It can also be said that diabetic neuropathy is not considered primarily a disorder in regeneration; consequently the teaching of Hansson et al (1986) should have no conclusive bearing on it. While regenerating axons (sprouting) are seen in diabetic nerve, diabetic neuropathy involves a constellation of symptoms, and no known or accepted relationship exists between these symptoms and regeneration. In the classic textbook "Peripheral Neuropathy, 2nd edition" by Dyck et al, W. B. Saunders Co, Philadelphia, 1984 the topic of Diabetic Neuropathy (Chapter 76) is carefully reviewed by Thomas and Eliasson (pp 1773–1810). They list the various theories as to causation of neuropathy (Table 76-4) and include vascular (microangiopathy, atherosclerosis, intraluminal fibrin deposition), mechanical (abnormal susceptibility to pressure), and metabolic (vitamin deficiency, lipid abnormalities, sorbitol accumulation, myo-inositol deficiency, abnormal glycosylation, impaired synthesis of structural proteins, and diketone toxicity) disturbances as the main theories. None of these theories has as its basis a failure in regeneration. For example, one theory contends that hyperglycemia results in increased sorbitol accumulation, and this sugar may result in abnormal glycosylation and impaired synthesis of structural proteins. Therefore to those skilled in this art a relationship between diabetic neuropathy and the regeneration is not evident. The relationship to the "regeneration" of Hansson et al (1986) would be even more obscure. Therefore, it should not be considered as a given that, from the teachings of Hansson et al (1986), IGF-I obviously has a use in the treatment of neuropathy, particularly diabetic neuropathy.

For example, there are many symptoms in diabetic neuropathy with no known or generally accepted relationship to regeneration. For example, microangiopathy, accumulation of sorbitol in nerves, depletion of myo-inositol, abnormal glycosylation, diketone toxicity, ischemia of nerves, decline in conduction velocity in nerves, are among some of the many changes in the biochemical mileau unrelated in any known or accepted way to regeneration. Even if IGF-I were to increase regeneration, there is no basis to believe that neuropathy due to diketone toxicity, ischemia, abnormal glycosylation, etc. would be alleviated. Therefore the relationship between IGF-I and "regeneration" of Hansson et al (1986) does not teach whether IGF-I is useful for treatment or repair of important syndromes of diabetic neuropathy.

Moreover, Hansson et al (1986) does not teach whether IGF-I would have utility even in the more limited sphere concerned with the treatment of regeneration in neuropathy, particularly diabetic neuropathy. Hansson et al (1986) did not study regeneration within the context of neuropathy. Given the abnormal biochemical mileau in diabetes one may not know a priori whether IGF-I could increase regeneration following trauma in diabetes. To those skilled in the art, accumulation of the sugar sorbitol in nerve tissues is believed to be the major cause of diabetic neuropathy (Sima et al., 1988 New Eng J Med 319: 548–55). Aldose reductase inhibitors reduce sorbitol content in nerves, and there is a resultant increase in numbers of regenerating nerve fibers. These authors state, "These findings suggest that hyperglycemia, through its activation of the sorbitol pathway in one or more peripheral-nerve cells, plays an active and continuing role in progressive nerve-polyneuropathy." This interpretation suggests that the normal repair and regeneration due to IGF-I would be blunted so long as sorbitol is high in diabetes. There is no known relationship between IGF-I and sorbitol content, and under this theory IGF-I could not alter the process of nerve regeneration. There is direct evidence which shows that the increase in IGF-I following crush (Hansson et al, 1986) does not produce the same regeneration in diabetic rats as in normal rats. Following nerve crush, both the onset (Bisby, 1980 Exptl. Neurol. 69: 74–84) and rate (Ekstrom and Tomlinson, 1989 J. Neurol. Sci. 93: 231–237) of regeneration are found to be severely impaired in diabetic rats. The presence of inhibitors of IGFs in diabetic serum was previously discussed. Thus, one may not know, a priori, whether exogenous IGF-I would be efficacious for regeneration in the abnormal biochemical mileau of diabetic neuropathy. And even if IGF-I were efficacious, the relationship of regeneration to the other severe symptoms which comprise the syndrome of diabetic neuropathy is obscure. Moreover, any relationship to the "regeneration" of Hansson et al (1986) would be even more remote.

Thus, in summarizing the state of the prior art, it can be said that applicant's theory, in vitro studies, IGF-II gene expression studies and the Hansson et al (1986) reference, when taken alone or in conjunction, teach or suggest that IGFs can ameliorate damage to nerve cells, as well as heal and/or repair nerve cells in vivo, particularly in neuropathies such as diabetic neuropathy. For example, applicant has studied this problem, and in the Description of Drawings and Preferred Embodiments (Table 1, FIG. 12), shows that IGF-II locally infused near the sciatic nerve can prevent the impairment of conduction velocity in diabetic rats. These results are statistically significant in Lewis ($P<0.02$, $N=4$ rats) and Sprague-Dawley ($P<0.001$, $N=3,4$) rats.

This invention is based in large part on Applicant's novel theory that IGFs play a role in diabetic neuropathy. Unlike all other theories, which are based on metabolic disturbances secondary to hyperglycemia, Applicant's theory is independent of hyperglycemia. A prediction of Applicant's theory is that IGF-II can prevent diabetic neuropathy, despite hyperglycemia. In Table 2, it is shown that IGF-II can indeed prevent impairment of conduction velocity, despite continued hyperglycemia in diabetic rats. These results provide further validation of applicant's theory.

The mechanism by which IGF-II prevents impairment of conduction velocity in diabetes is not presently known. This impairment comes well before any known decrease in axonal calibers. Various experts believe that there is a decline in sodium/potassium ATPase in diabetes. The loss of sodium current in the action potential would lead to a decline in conduction velocity. There is no known correlation between regeneration and conduction velocity. Tetrodotoxin binds to sodium channels and blocks the action potential and conduction velocity. However, tetrodotoxin does not prevent the regeneration and growth of axons. Therefore, conduction velocity and nerve regeneration are independent of one another. The effect of IGF-I on "regeneration" (Hansson et al., 1986) should not constitute prior art on effect of IGF-I on conduction velocity, particularly in neuropathy.

Likewise, the effect of IGF-II on conduction velocity does not reveal whether IGF-II or IGF-I would be efficacious on regeneration in diabetes.

The independent problem of whether IGF-II can Support regeneration in vivo has been studied by the Applicant. Applicant is of the opinion that neither his theory, in vitro studies, gene expression studies with IGF-II, nor Hansson et al (1986) constitute prior art as to whether IGFs can support regeneration in vivo. Under the Description of Drawings (Table 3), applicant shows that IGF-II locally infused at 1 ug/ml can increase sciatic nerve regeneration following crush. These results for IGF-II are statistically significant (P<0.0001, N=6,3 rats). These results show for the first time that endogenous IGF-II can increase regeneration in vivo.

Taken together, these data have provided applicant with a significant base on which to consider the direct effects of insulin, IGF-I, IGF-II, protein kinase C, and other neurotrophic factors such as NGF on the nervous system, and indicates their usefulness in ameliorating damage to neurons in diabetes, and in accelerating healing and/or repair in damaged nerve cells.

DESCRIPTION OF THE TABLES AND DRAWINGS

Table 1 shows that locally infused IGF-II does, but insulin does not, increase conduction velocities in sciatic nerves of diabetic rats.

| Treatment | N | Conduction Velocity (m/sec) | |
|---|---|---|---|
| | | Left | Right |
| Part A. Lewis nondiabetic | | | |
| No pump | 4 | n.d. | 82.0 ± 1.2 |
| Vehicle | 4 | 80.9 ± 2.2 | 81.7 ± 1.8 |
| Diabetic | | | |
| No pump | 4 | n.d. | 71.9 ± 3.3* |
| Vehicle | 4 | 72.1 ± 2.0† | 71.8 ± 3.5† |
| IGF-II, 100 µg/ml | 4 | 76.3 ± 2.9‡ | 70.3 ± 3.3§ |
| Insulin, 100 µg/ml | 3 | 73.1 ± 1.0§ | 73.4 ± 1.1§ |
| Part B. Sprague-Dawley Nondiabetic | | | |
| No pump | 4 | 81.9 ± 1.4 | 82.2 ± 1.2 |
| Vehicle | 3 | 31.5 ± 2.0 | 80.1 ± 2.4 |

Diabetic and nondiabetic rats received no pumps, or were implanted with miniosmotic pumps which delivered vehicle (RPMI 1640 medium), IGF-II, or insulin through a catheter placed close to the left sciatic nerve. After 7 days, the conduction velocity was measured in both the left and right sciatic nerves. Values are means±SD (N, number of rats). N.d., not determined.

*P<0.005 between right sides of nondiabetic vs diabetic Lewis groups without pumps.

†P<0.005; nondiabetic vs diabetic Lewis groups treated with vehicle. Comparisons between corresponding left or right sides of groups.

‡P<0.025; 100 µg/ml IGF-II vehicle-treated diabetic Lewis groups. Comparison between left (pump) sides.

§No significant difference; 100 µg/ml IGF-II, or insulin, vs vehicle-treated Lewis diabetic groups. Comparisons between corresponding left or right sides.

Table 2 shows locally infused IGF-II does not reduce hyperglycemia in serum of diabetic rats, despite prevention or neuropathy.

| Treatment | N | Glucose (mg/dl) | |
|---|---|---|---|
| | | Day 1 | Day 7 |
| A. Lewis Nondiabetic | | | |
| No pump | 4 | 137 ± 8 | 144 ± 10 |
| Vehicle | 4 | 145 ± 4 | 151 ± 7 |
| Diabetic | | | |
| No pump | 4 | 476 ± 20* | 617 ± 115* |
| Vehicle | 4 | 540 ± 21† | 507 ± 5† |
| IGF-II, 100 µg/ml | 4 | 568 ± 56‡,§ | 542 ± 72‡,§ |
| insulin, 100 µg/ml | 3 | 487 ± 61‡,§ | 596 ± 43‡ |
| B. Sprague-Dawley Nondiabetic | | | |
| No pump | 4 | n.d. | n.d. |
| Vehicle | 3 | 132 ± 25 | 145 ± 9 |
| Diabetic | | | |
| No pump | 4 | 529 ± 67 | 545 ± 40 |
| Vehicle | 5 | 505 ± 40† | 479 ± 30† |
| IGF-II, 300 µg/ml | 4 | 545 ± 77‡,§ | 547 ± 96‡,§ |

Figure 12:
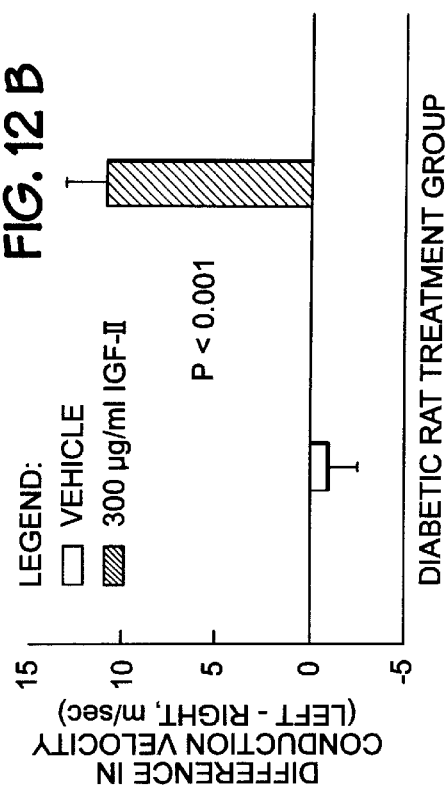
Figure 12:

Rats were treated as described in the legends to Table I and FIG. 12. On Days 1 and 7 post-surgery, blood samples were withdrawn for determination of serum glucose concentrations. Values are means±SD (N, number of rats). N.d., not determined because measurements were available from a previous study in an identically matched group (see text). Statistical comparisons were made between groups on corresponding Days 1 or 7.

*P<0.005; diabetic vs nondiabetic groups, both without pumps.

†P<0.001; diabetic vs nondiabetic vehicle-treated groups.

‡P<0.001; diabetic group treated with IGF-II vs nondiabetic group treated with vehicle.

§No significant difference; IGF-II, or insulin, vs vehicle-treated diabetic groups.

Table 3 shows at 1 µg/ml IGF-II increases regeneration of sensory axons in crushed sciatic nerves ot rats.

| Treatment | Regeneration Distance (mm) | |
|---|---|---|
| RPMI | 4.67 ± 0.41 | (N = 6) |
| IGF-II | | |
| 1 ± µg/ml | 6.50 ± 0.00 | (N = 3)* |
| 10 ± µg/ml | 6.50 | (N = 1) |

Rats (12-week-olds) were randomly assigned to treatment groups. The left sciatic nerves were crushed as described in the text. Miniosmotic pumps released either RPMI 1640 vehicle or IGF-II close to the site of crush, as indicated in the table. Four days later, the distance of regeneration was measured by the pinch test. The values are means and S.D. The number of rats in each group is shown in parenthesis.

*P<0.001 between group treated with 1 µ/ml IGF-II vs RPMI vehicle.

These results show that IGF-II increased regeneration at 1 µg/ml.

FIG. 1 plots insulin concentration versus an AUC (area under curve) with respect to certain scannings of autoradiograms (Northern blots) on a densitometer. It shows insulin can increase the relative abundance of 68 and 170 kD neurofilament protein mRNAs in SH-SY5Y cells.

Figure 2:
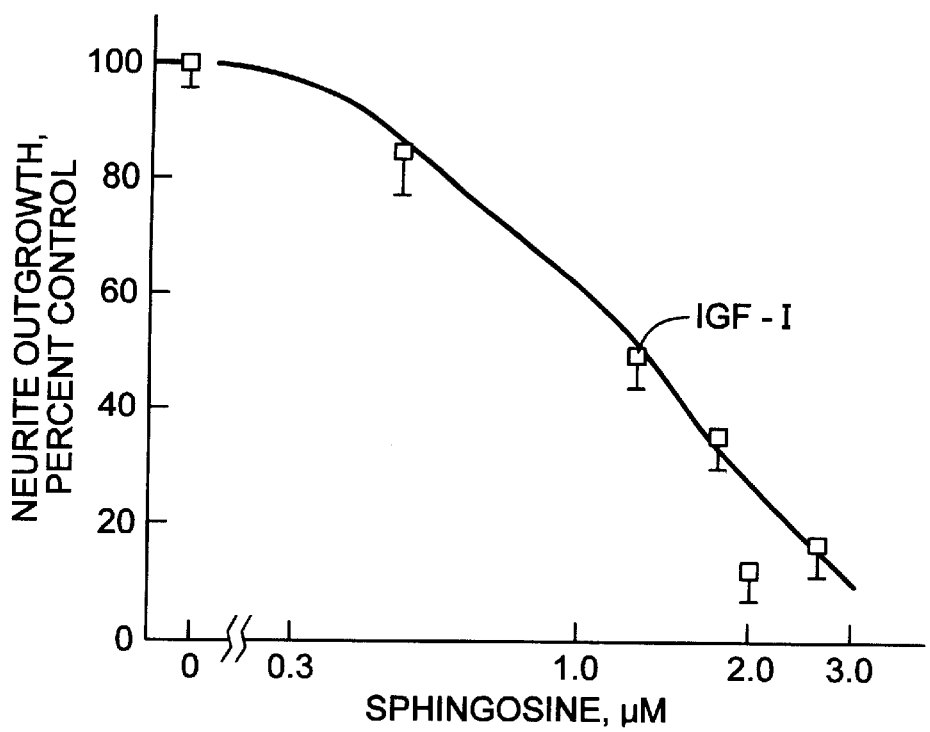
Figure 2:
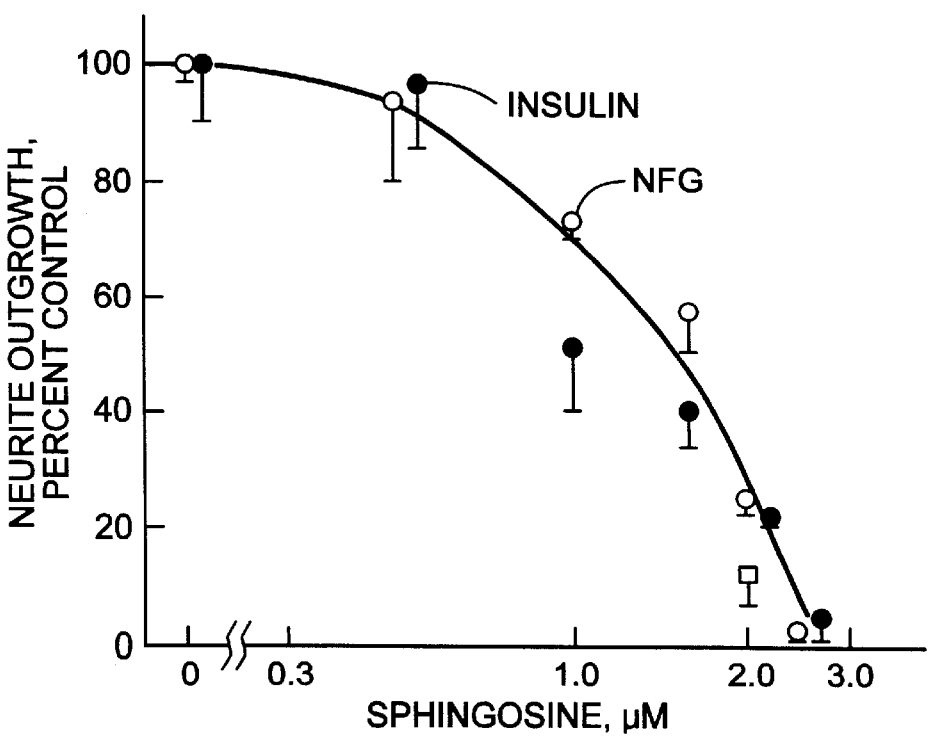

FIG. 2 plots neurite outgrowth directed by IGF-I (Part A), NGF and insulin (Part B) versus sphingosine concentration. It shows that sphingosine can inhibit neurite outgrowth directed by each of these factors with the same sensitivity in cultured spinal cord neurons of a rat, and that a common step is being inhibited.

Figure 3:
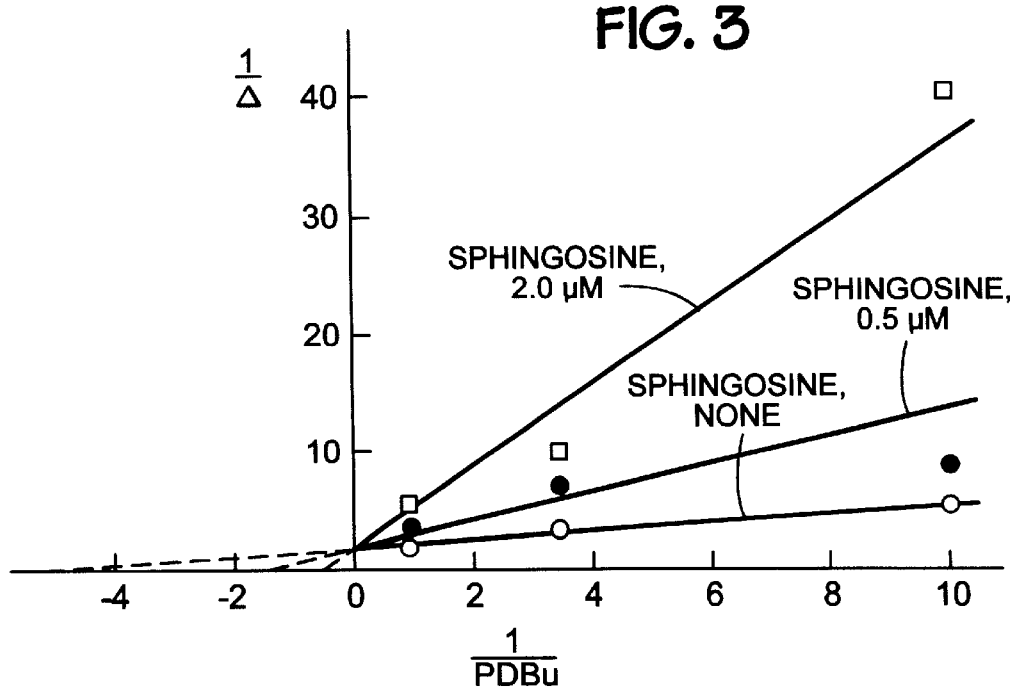

FIG. 3 plots the reciprocal of the neurite outgrowth response in SH-SY5Y cells versus the reciprocal of the concentration of phorbol-12,13-dibutyrate (PDBu) in the presence of several concentrations of sphingosine. It shows that neurite growth stimulated by PDBu, which is a phorbol ester tumor promoter and activator of protein kinase C, is competitively inhibited by sphingosine, which is a competitive inhibitor of protein kinase C.

Figure 4:
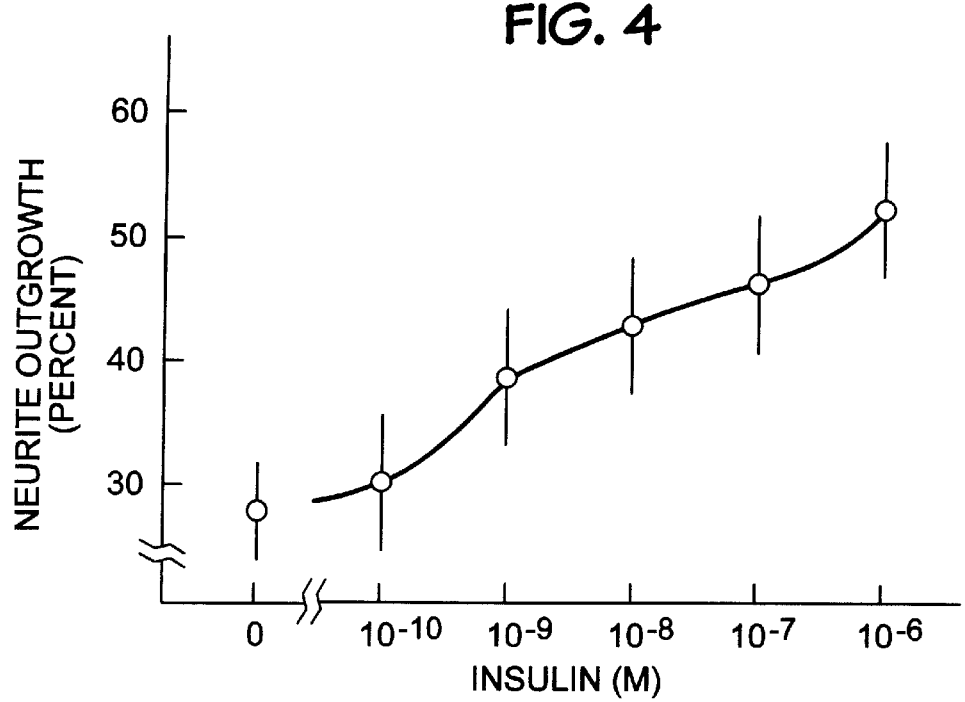

FIG. 4 plots neurite outgrowth versus insulin concentration. It shows that physiological concentrations of insulin can stimulate neurite formation in cultured spinal cord cells from embryonic 17 day old rats.

Figure 5:
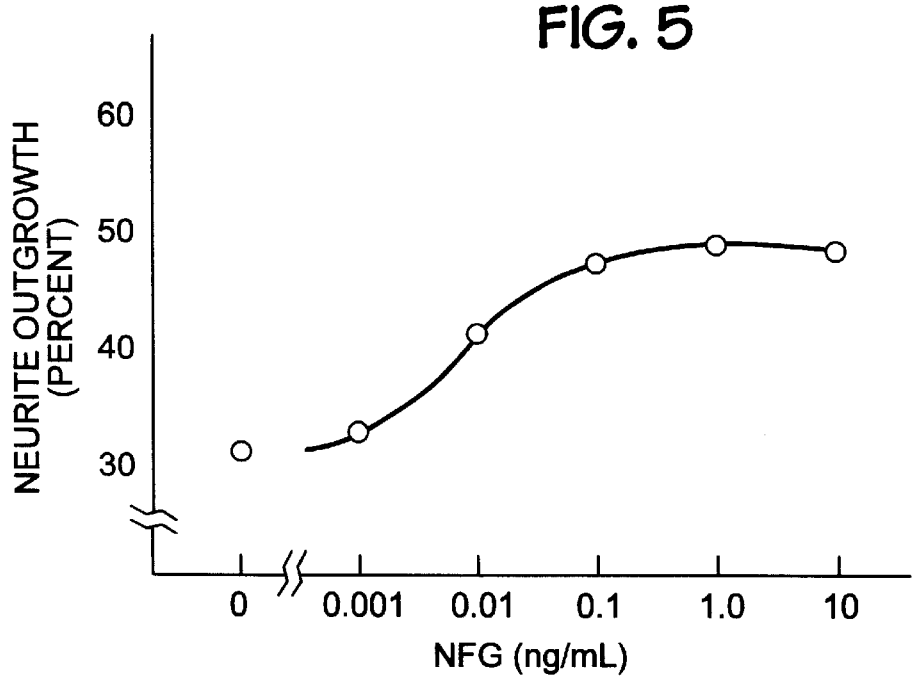

FIG. 5 plots neurite outgrowth versus NGF concentration. It shows that physiological concentrations of NGF can stimulate neurite formation in cultured spinal cord cells from embryonic 17 day old rats.

Figure 6:
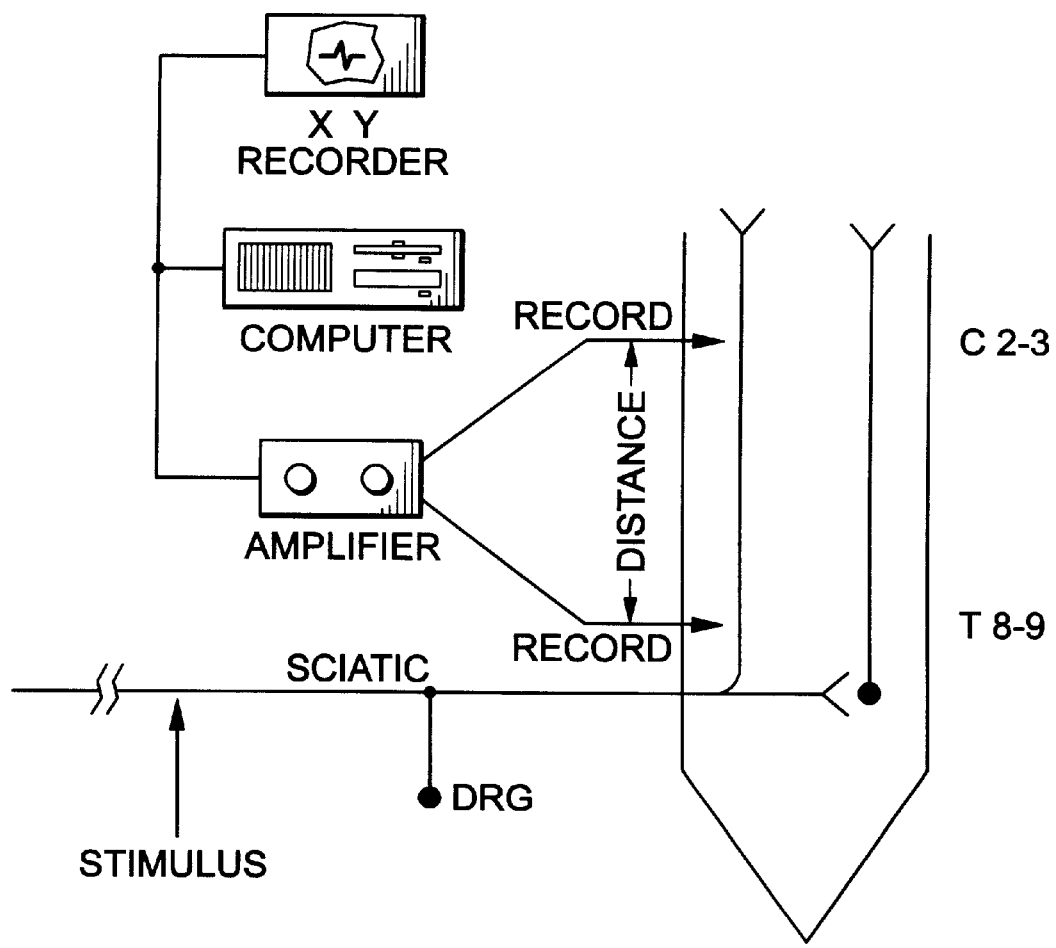

FIG. 6 is a schematic of a device for measuring spinal cord evoked potentials, especially in the rat.

Figure 7:
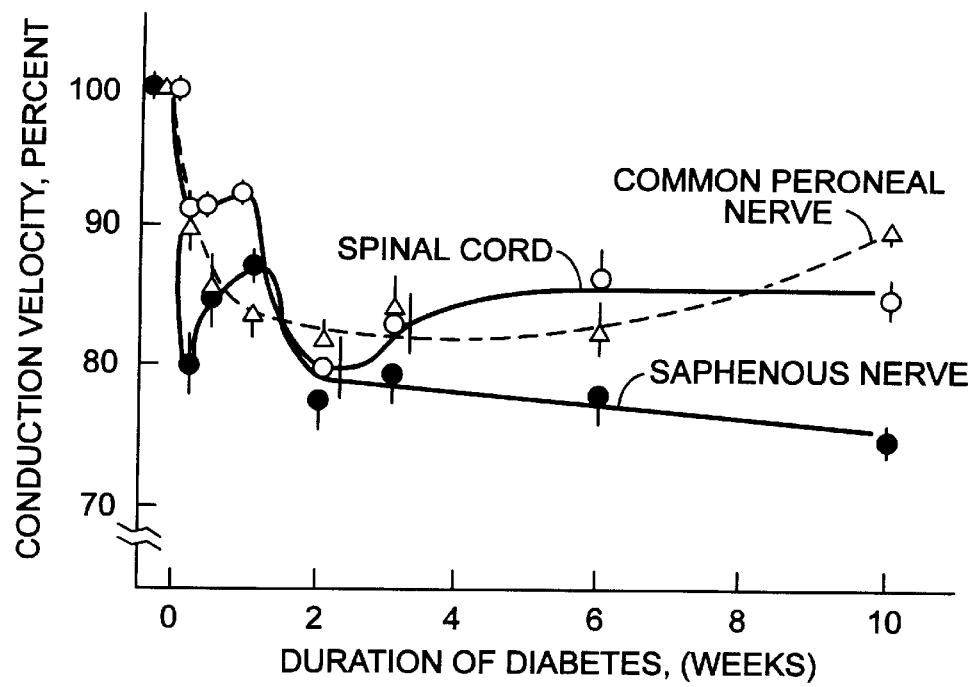

FIG. 7 plots conduction velocity versus duration of diabetes. It shows that conduction velocity is decreased in the spinal cords of diabetic rats. It shows that the kinetics of conduction velocity decline in spinal cord, saphenous nerve and common peroneal nerve are very similar during the first two weeks, suggesting a common mechanism.

Figure 8:
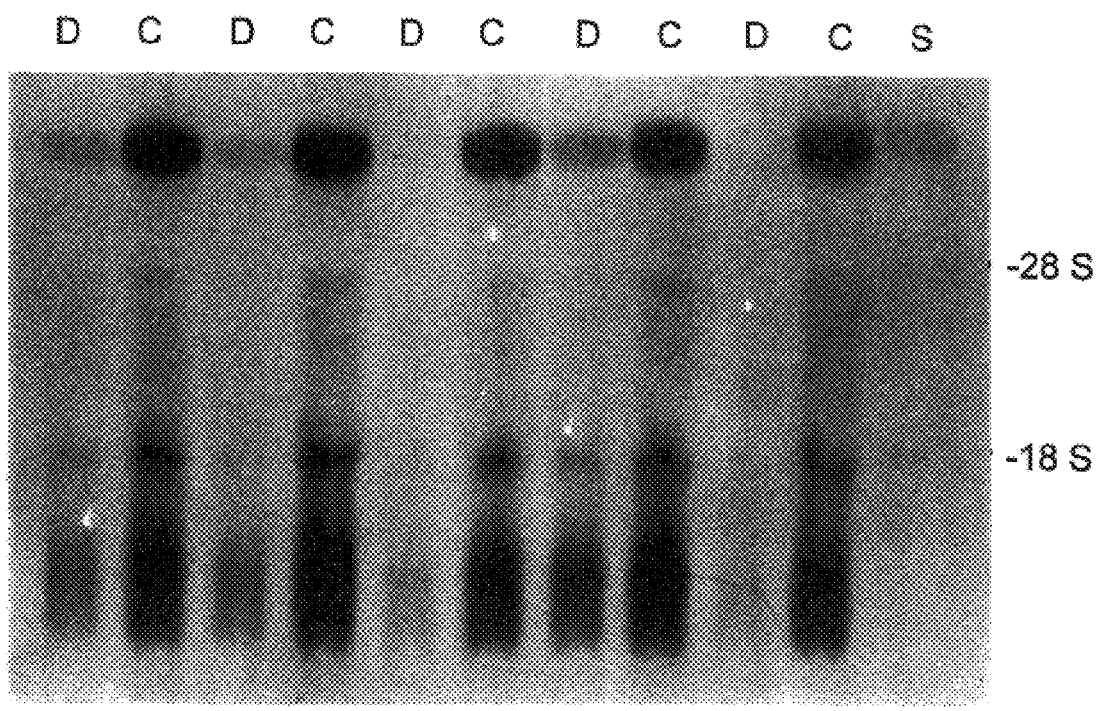

FIG. 8 depicts the results of an autoradiogram (Northern blot) which shows the relative abundance of IGF-I mRNA in liver from 13-week-old rats either untreated (C) or diabetic for 1 week (D). (S), skeletal muscle RNA from 4-day-old rat. It shows that the abundance of IGF-I mRNA is sharply reduced in diabetic rats.

Figure 9:
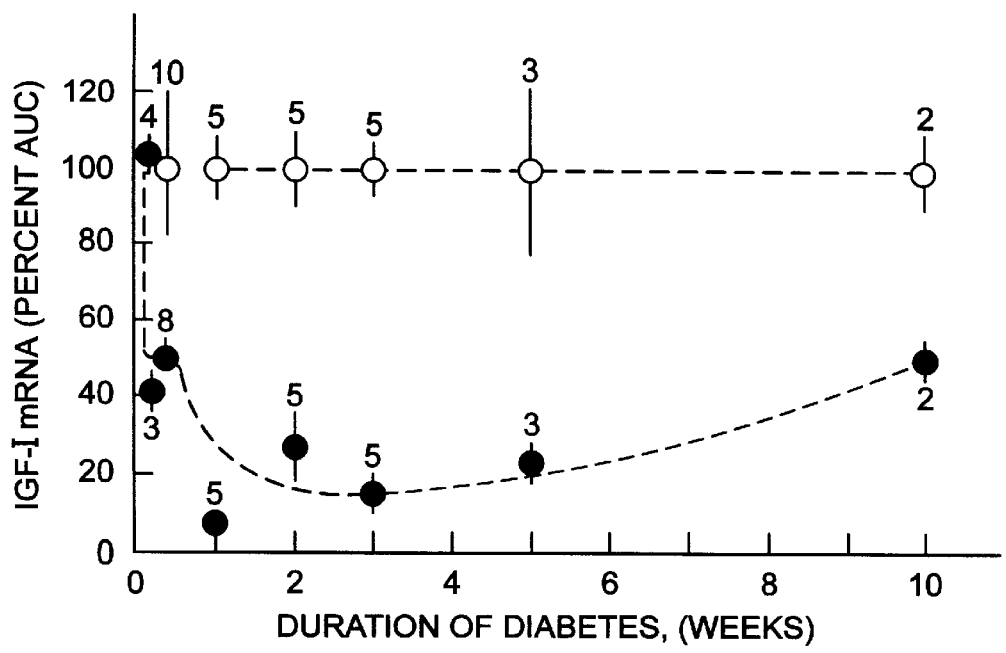

FIG. 9 plots IGF-I mRNA (% AUC) versus duration of diabetes. It shows the kinetics of decline of IGF-I mRNA in liver from streptozotocin diabetic rats. Note that these kinetics are closely correlated with the kinetics for decline in conduction velocity in spinal cord and peripheral nerves (FIG. 7). For the reasons discussed in the text, this greatly strengthens the argument that IGFs may play a role in regulating the function of central and peripheral neurons in diabetes.

FIG. 10 shows (A) an autoradiogram result of a Northern blot depicting the abundance of IGF-II mRNA in skeletal muscle as a function of rat age, (B) the plot of both IGF-II mRNA (AUC) abundance in muscle, and percentage of muscle fibers with multiple synapses, versus rat age, and (C) Oligo dT hybridized (AUC) to the same samples of muscle RNA versus rat age. They show that down regulation of IGF-II mRNA levels is correlated with the developmental loss of multiple synapses in rat skeletal muscle. They also show this effect is selective because the relative pool of total mRNA is, in contrast, increasing over the same developmental period.

Figure 11:
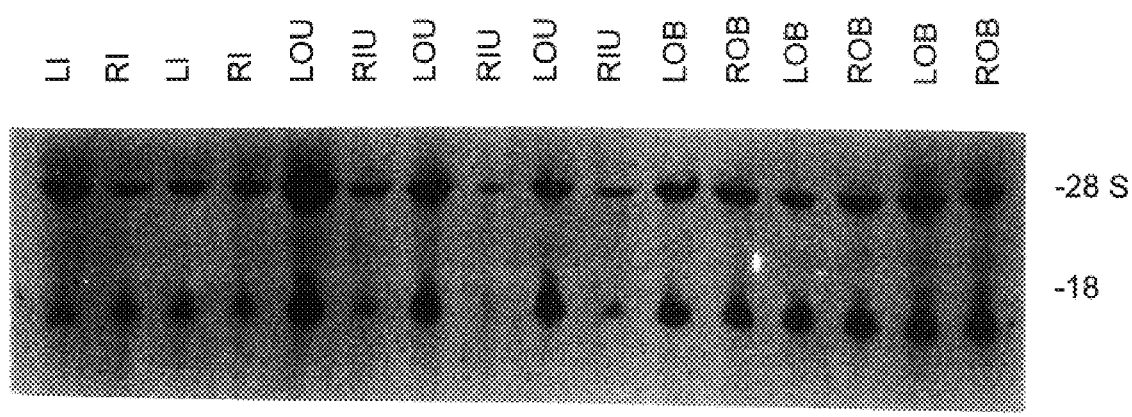

FIG. 11 shows the results of an autoradiogram (Northern blot) depicting the abundance of IGF-II mRNA in RNA from the left (L) and right (R) hind leg muscles of rats. The nerve supply to the muscle were either intact (I) or transected (O). Transection was either unilateral (U) or bilateral (B). The Figure shows that IGF-II gene expression in muscle is increased following denervation. Together with the results of FIG. 10, the data shows that the maturation of neuromuscular synapses provides a signal inhibitory to the expression of the IGF-II gene in muscle. Nerve transection relives the inhibition, and the increased IGF-II mRNA levels support the repair of damage nerve.

FIG. 12 shows that infused IGF-II can prevent impairment of conduction velocity in diabetic rats. Diabetic rats were implanted with miniosmotic pumps which delivered vehicle (RPMI 1640 medium) or IGF-II close to the left sciatic nerve in rats. Seven days later, the conduction velocity was measured in both the left treated and right untreated sciatic nerves in each rat, and the difference (left-right) was calculated. In this pairwise comparison, each rat serves as its own internal control, and avoids the potential for individual differences between animals. The values are means±S.D. There were 4 rats in each group, except in the vehicle-treated Sprague-Dawley group where N was 3. There were significant positive differences in (left-right) conduction velocity of both Lewis and Sprague-Dawley rats treated with IGF-II vs vehicle. The positive differences showed that the conduction velocity in each case was faster in the left nerve, which was closer to the site of IGF-II infusion.

Figure 13:
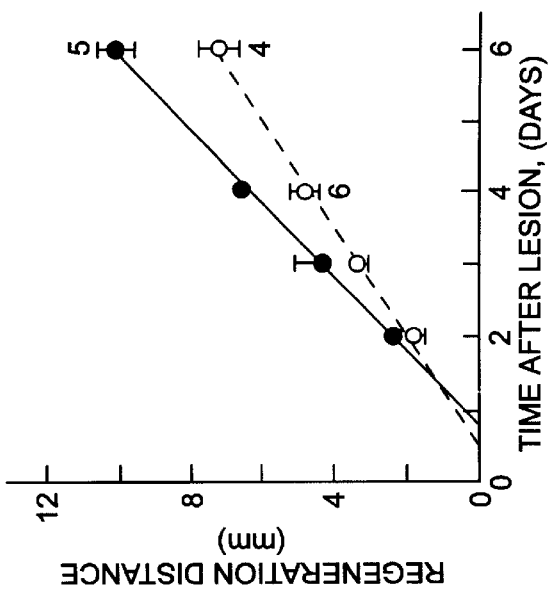

FIG. 13 shows that infused IGF-II increases the rate of sensory nerve regeneration following crush of the sciatic nerve in rats. The regeneration distance is plotted against the time after nerve crush. The open symbols show the effect of local infusion of vehicle (RPMI 1640 medium) near the crushed nerve. The closed symbols show the effect of infusion of 1 $\mu$g/ml IGF-II. The values are means±S.D. (N=3 rats, else N is shown in the graph). Where S.D. is smaller than the symbol, it is not shown. This figure shows the IGF-II increased the rate of regeneneration 47% over the spontaneous regeneration, but the onset of regeneration was not affected.

DESCRIPTION OF THE PREFERRED EMBODIMENTS

The processes and/or therapeutic agents of this patent disclosure particularly emphasize the use of insulin, human IGF-I (aka Somatomedin A or Somatomedin C), and/or IGF-II (aka Multiplication-stimulating-factor). Moreover each of these ingredients can be used in combination with neurotrophic factors, and compounds which activate protein kinase C. These capabilities were demonstrated in several ways. For example, for reasons more fully discussed in later portions of this patent disclosure, FIG. 2 shows that sphingosine can inhibit with the same sensitivity, NGF, insulin, and IGF-I directed neurite formation in sympathetic neurons. This indicates a common step is being inhibited. It should first be noted that the experiment which established this point were carried out under culture conditions which were the same as those described in the Recio-Pinto et al., 1986 reference. In any event, the inhibition achieved was reversible on washout of sphingosine. These particular experiments did not however exclude the potential that sphingosine is inhibiting at a locus other than protein kinase C. For that reason the experiment which resulted in FIG. 3 was conducted; it shows that neurite outgrowth induced by phorbol dibuturate (PDBu) was competitively inhibited by sphingosine in SH-SY5Y cells. This showed that sphingosine inhibition is clearly as protein kinase C. The general conditions of the experiment were as described in the Spinelli and Ishii, 1983 reference. In any event, it should also be noted that protein kinase C appears to act in a distal part of the pathway because the capacity of NGF and insulin to elevate tubulin mRNA was not inhibited by sphingosine. Thus, it can be concluded that activators of protein kinase C may be useful to stimulate the effects of insulin, IGFs and NGF.

The results of several other tests conducted by applicant also bear out the predictions of, and provide strong support for, the theory proposed. For example, applicant established that physiological concentrations of insulin can increase neurofilament 68 kDa and 170 kDa and mRNAs levels (see FIG. 1). In order to conduct this test, human SH-SY5Y cells were incubated for 2 days in the presence of various concentrations of insulin in RPMI 1640 medium under the conditions previously established (Mill et al., 1985). Poly $(A)^+$ RNA was purified and equivalent amounts (6 ug) electrophoresed in 0.8% agarose gels containing formaldehyde. Following transfer to nitrocellulose, the samples were hybridized at high stringency (final wash 45–50 min in 0.5 SSC at 68° C., as described in the Fernyhough and Ishii, 1987 reference) to a nick-translated cDNA containing the coding sequence of human 68 kDa neurofilament protein (1.6 kb insert). Subsequently, the nitrocellulose blot was boiled and rehybridized at the same high stringency to a nick-translated cDNA containing the coding sequence of human 170 kDa neurofilament protein (1.0 kb insert). Autoradiograms were scanned on a densitometer and the area under the curve (AUC) for each sample was determined. The relative AUC values are shown. The details of the methods employed are described in (Mill et al., 1985; Fernyhough and Ishii, 1987). Similar results were obtained in response to IGF-I. These results show that insulin and IGFs can regulate neurofilament gene expression, and further extend Applicant's hypothesis that they share with NGF similar effects and mechanisms. The increase in the abundance of these transcripts also may stimulate microtubule and neurofilaments formation, thereby contributing to axon grown and maturation.

Other pertinent aspects of axonal maturation were also considered. For example, the effects of insulin on the firing frequency of neurons, neurotransmitter biosynthesis, and uptake of neurotransmitters was studied. It was found that pheochromocytoma PC12 cells are not electrically excitable in the basal state, but stimulation with NGF leads to the appearance of action potentials together with the induction of voltage-sensitive $Na^+$ and $Ca^{++}$ channels. NGF can modify neurotransmitter content and the activity of enzymes involved in their synthesis. With respect to NGF, it is also important to note that it is important to the development and maintenance of the vertebrate nervous system. Its administration can cause hypertrophy and hyperplasia of sensory and sympathetic ganglia, whereas the anti-NGF antiserum can cause profound destruction of these ganglia when administered early in development. In older vertebrates, this antiserum is less harmful to sensory ganglia but retains its toxicity against the sympathetic nervous system. Brain and spinal cord neurons are also responsive to NGF. It is not a mitogen, and the hyperplasia produced by its administration results from rescue of developmentally programmed neuronal cell death. Neurite growth follows the concentration gradient of NGF, as shown experimentally in vitro and in vivo. Current models suggest NGF and/or other neurotrophic factors are produced and released by target tissues and may guide neurite growth up a concentration gradient. Because NGF is required by certain neurons during a critical period in development, extraneous neurons not receiving a supply of the factor, possibly through retrograde axonal transport would tend to be pruned. It has previously been shown that the activity of NGF can be regulated by insulin and IGFs (see generally Recio-Pinto et al. Proc. Natl. Acad. Sci. USA 81, 2562–2566, 1984). Applicant has however also shown that NGF can support neurite growth in spinal cord cells (FIG. 5). Therefore, a decline in insulin and IGF activity in diabetes may be expected to diminish the activity of NGF and these events together are postulated to contribute to neuropathy observed in the spinal cord and peripheral nerves (FIG. 7).

Because insulin receptors are present in the central nervous system, it was anticipated that insulin might mediate neurite formation in spinal cord cells. FIG. 4 shows that physiological concentrations of insulin can increase neurite formation in cultured spinal cord cells obtained from 17-day-old embryonic rats. The spinal cords were removed, incubated with 0.5% trypsin, then gently passed through a wire mesh screen to produce a suspension of single cells. The cells were counted and plated at a density of 100,000 cells in 2 ml of media comprised of 1:1 Ham's F12-Dulbecco's Modified Eagle's Medium with 2% fetal calf and 2% horse serum on polylysine coated dishes. After 2 days, the proportion of cells with neurites was counted. Concentrations below 1 nM insulin were active. Consistent with the cross-occupancy of insulin into IGF receptors, supraphysiological concentrations of insulin caused additional neurite outgrowth. The broad dose-response curve is consistent with the broad dose-response curves for increasing tubulin mRNA levels and occupancy of insulin receptors in other neuronal cell types. The plating efficiency was about 60%. In addition, physiological concentrations of NGF induced neurites under the same conditions of culture (see FIG. 5). These observations are of importance when considered together with the demonstration that diabetes can induce neuropathy in the spinal cord.

This finding led to Applicant's subsequent prediction that insulin ablation might cause a functional neuropathy in the spinal cord. In order to test this prediction, a procedure to measure evoked spinal cord potentials was developed. It was found that conduction velocity is indeed significantly reduced in streptozotocin diabetic rats. Heretofore, reduction of spinal cord conduction velocity has not been observed in experimental or clinical diabetes. FIG. 6 shows the general scheme of the measurement. The sciatic nerve (ischiatic branch) was stimulated and recording electrodes were placed at spinal cord levels T8-9 and C2-3. The most rapidly conducting fibers gave rise to the earliest peaks in the compound action potentials. For the most rapidly conducting fibers, the interval between the stimulation artifact and the onset of the first negative peak represents the conduction time between stimulation and recording sites. This interval is longer at the more distal recording site C2-3 than at T8-9. The difference in latencies measured at the two recording sites was divided by the measured distance between the recording electrodes to permit calculation of the conduction velocity within the cord. The conduction velocity was invariant in normal male rats between 12 (47.3±1.1 m/s, N=5) and 22 (49.3±2.7 m/s, N=5) weeks of age. FIG. 7 shows the effects of duration of diabetes on relative conduction velocities in spinal cord, saphenous nerve, and common peroneal nerve following the onset of diabetes in 12-week-old male rats.

In order to conduct this experiment, male Sprague-Dawley rats were randomly assigned into treatment groups, fasted overnight, anesthetized with 80 mg/kg ketamine and 0.3 mg/kg acepromazine, i.m., and one treatment group was injected with 40 mg/kg streptozotocin i.v. to induce diabetes.

Serum glucose concentrations were determined the following day using Sigma glucose diagnostic kit 510. Sigma Chemical, St. Louis, Mo. Only diabetic rats with greater than 22 mM glucose were recruited for the study. On various experimental days, as indicated in FIG. 7, groups of 5–6 animals were fasted 16 hours and anesthetized with a combination of 50 mg/kg ketamine and 20 mg/kg xylazine i.p. Depth of anesthesia was monitored, and supplemental 25 mg/kg ketamine i.m. was given as needed. Blood was drawn for glucose determination, and the animals prepared for the measurement of spinal cord and peripheral nerve conduction velocity. Body temperature was maintained within 1° C. of normal using a circulating water blanket. The conduction velocities are expressed in percentages relative to values in age-matched untreated animals. In fulfillment of the prediction, conduction velocity was reduced in the spinal cord of diabetic rats. The decline in spinal cord conduction velocity was not due to streptozotocin toxicity, because the implantation of miniosmotic pumps which released insulin at a constant rate for 7 days (10 units/kg body weight/day) prevented the decrease in conduction velocity in spinal cords of streptozotocin diabetic rats. The kinetics of decline in conduction velocity were very similar in both spinal cord and peripheral nerves, indicating a common mechanism. It is particularly revealing that there was a biphasic decline in spinal cord and saphenous nerve conduction velocity. As will be shown below these kinetics correlate closely with the decline in IGF-I mRNA levels. These findings are consistent with the observed reduction in perikaryal volume of anterior horn motor and sensory neurons in diabetic rats. Moreover, they are consistent with the data in FIG. 4 showing insulin can support neurite formation in cultured spinal cord neurons.

Although the prior art reveals degeneration of spinal cord tracts in long-standing clinical diabetes, such observations have remained inconclusive because the degeneration might arise secondarily from the debilitating effects of age together with the accumulation of many years of diabetic distress. But, when considered together with Applicant's finding that spinal cord conduction velocity can rapidly fall off (statistically significant decline within a few days), the present understanding of the extent of clinical pathology in the central nervous system appears starkly inadequate. Delayed evoked responses in the auditory brainstem of patients have been measured.

Because multiple neurotrophic factors may act on a population of neurons, reduced insulin activity alone may be insufficient to produce the major changes associated with neuropathy. This consideration led to the important prediction that a decline in activity of neurotrophic factors (in addition to insulin) might coincide or precede the decline in conduction velocity in the diabetic rat. The prediction was tested as shown in FIG. 8. Since primary source of IGF-I in the circulation is known to be the liver, the potential that diabetes could affect IGF-I mRNA levels was studied. Rats (12-weeks-old) were randomly assigned into two treatment groups, and one group was injected with streptozotocin as before to induce diabetes. Streptozotocin selectively destroys the beta cells of the pancreas to inhibit insulin production. One week later RNA was isolated from the livers of treated and untreated rats, and equivalent amounts (40 ug) from each sample were electrophoresed in 0.8% agarose gels containing formaldehyde. Ethidium bromide staining confirmed that equal amounts of undegraded RNA was present in each lane, and revealed the presence of 18 and 28S rRNA bands. Following transfer to nitro-cellulose, the samples were hybridized to a nick-translated cDNA containing the coding sequence of rat IGF-I (a 685 nucleotide insert containing the pre-pro-IGF-I coding sequence, 69 nucleotides of the 3' noncoding sequence and 340 nucleotides of the 5' sequences. A print of the autoradiogram is shown wherein C represents as untreated control; D, diabetic; and S, skeletal muscle RNA from a 4-day-old rat. Although derived from a unique gene, several mRNA bands are revealed due to the presence of two promoters, alternatives splicing, and alternative polyadenylation. The same bands have been detected in rat liver by others (Murphy et al., Endocrinology 120: 1279, 1987). A resulting autoradiogram was scanned on a densitometer, and the IGF-I mRNA level was significantly lower in diabetic animals: 1407±306, untreated; 93±68, diabetic; P<0.0005. These relative AUC values are means±SEM (N=5 animals). The same samples (8 ug per lane) were additionally analyzed on slot blots. The filter was successively hybridized to $^{32}$-P-labeled coding region clone pMH921 (Brown et al. Mol Cell Biol 5:2879, 1985), and oligo(dT), to detect histone 3.3 mRNA and total mRNA, respectively. The procedure of Harley (Gene Anal Tech 4: 17, 1987) was used to end-label oligo(dT) and hybridize blots. The autoradiograms were scanned on a densiometer. The results showed that IGF-I mRNA per oligo(dT) was significantly decreased in diabetic animals: 1131±170, untreated; 82±24, diabetic. P<0.005. In contrast the histone 3.3 mRNA per oligo(dT) was not different between diabetic and untreated animals: 994±155, untreated; 769±152, diabetic. These relative AUC values are means ±SEM (N=5 samples run in duplicate). Therefore, IGF-I mRNA abundance is selectively decreased in diabetic liver. The effect is not confined to liver because, in other studies of the applicant, IGF-I mRNA, but not tubulin mRNA abundance, was significantly (P<0.005) decreased in adrenal glands from diabetic rats similarly treated. The decrease in IGF-I mRNA abundance was unlikely to be the result of a toxic effect of streptozotocin because the expression of other liver and adrenal genes were not similarly affected. Serum IGF-I levels also decline in pancreatectomized dogs and may be restored by insulin (Froesch et al, Adv Metab Disord 8: 237, 1975). The kinetics of the decline in IGF-I mRNA levels in liver (FIG. 9) was studied for purposes of comparison with the rate of development of conduction velocity deficits in diabetes. Rats (12-weeks-old) were randomly assigned into two treatment groups, and one group was injected with streptozotocin to induce diabetes. At various times thereafter, as indicated, groups of animals were assayed for IGF-I mRNA levels in liver, as described for FIG. 8. The values are means±SEM (number of animal in each group shown next to symbol) relative to AUC values from age-matched untreated rats. Where N=2 at 10 weeks, the values instead are ranges. The kinetics for the decline in IGF-I mRNA levels is remarkably similar and slightly precedes the decline in conduction velocity (FIG. 7). This striking correlation strongly suggests that IGF-I may play a role in the development of diabetic neuropathy, particularly in regulating conduction velocity in central and peripheral neurons.

Species differences in the regulation of neurotrophic factors might explain some of the variation in the pattern of emergence of clinical versus experimental neuropathy. In the case of the rat, there is a postnatal decline in IGF-II and increase in IGF-I activity. This means that the adult diabetic rat suffers a profound loss of insulin and IGF-I activity together with the developmentally sustained decline in IGF-II levels. This might explain the rapid and server neuropathy which follows the induction of diabetes in this specie. In contrast, IGF-II levels remain elevated after birth in humans.

IGF-I levels peak at puberty and slowly decline over several decades. This might explain why neuropathy is not as highly prevalent in juvenile type I diabetics as in streptozotocin diabetic rats. It should also be considered that clinical diabetes is seldom associated with so severe a loss in insulin activity as occurs in experimental diabetes.

One of the more important aspects of this patent disclosure is applicant's finding that the low insulin concentrations (about 1 nM) encountered during fasting can occupy a significant fraction of insulin receptors and readily support effects such as neurite outgrowth and survival. For example, applicant has found that concentrations as low as about 10 pM are active. Applicant has however also found that the occupancy of IGF receptors is correlated with neurite outgrowth. One site for IGF-II production is the chroid plexus and the leptomeninges from which IGF-II may be secreted into the cerebrospinal fluid. Similar to the classic neurotrophic hormone, NGF, a number of tissues including brain can produce IGF-I and IGF-II.

Heretofore, the mechanism regulating the developmental formation of neuromuscular synapses, and subsequent elimination of superfluous synapses, has not been understood. Applicant has however found that the developmental pattern of IGF-II gene expression in skeletal muscle is correlated with the formation and elimination of neuromuscular synapses.

The correlation with the formation of synapses is shown in FIG. 10. RNA was isolated from the calf muscles of littermate rats of the indicated ages. Following electrophoresis (40 ug per lane) in formaldehyde-agarose gels, ethidium bromide staining confirmed that equivalent amounts of undegraded RNA were present in each lane and showed the position of the rRNA bands. The RNA was transferred to nitro-cellulose and hybridized to the nick translated $^{32}$-P-labeled IGF-II cDNA clone 27 (The clone contains the entire coding sequence of the rat pre-pro-IGF-II cDNA). This clone and the hybridization procedure is described elsewhere (see generally Soares et al. Nucleic Acids Res 13: 1119, 1985). The autoradiogram is shown in FIG. 10, Part A.

There was a development down regulation of the IGF-II mRNAs in calf muscles. Several mRNA bands were evident. IGF-II, like IGF-I, is derived from a unique gene which gives rise to multiple transcripts due to differential splicing and polyadenylation (Soares et al., J Mol Biol 192: 737 1986). The autoradiogram was scanned on a densitometer and the ACU values are shown in FIG. 10, Part B, together with the data of Brown et al (J Physiol 261: 387, 1976) showing the developmental elimination of superfluous synapses. The developmental down regulation of IGF-II mRNA and elimination of superfluous synapses were exactly coincident. In contrast, the hybridization of oligo(dT) to the same samples, and to muscle RNA from a 63 day-old rat, showed that the abundance of total mRNA, estimated as hybridization of oligo-(dT), increased between postnatal 8 and 22 Days (FIG. 10, Part C). This is consistent with interpretation that the abundance of the total mRNA pool was increased relative to total RNA during rapid muscle growth. However, the amount of oligo(dT) hybridized to RNA from the 63 day-old rat was much lower than to RNA from 2 to 3-week-old rats, as might be expected following cessation of the growth spurt.

These results indicate that IGF-II transcripts were selectively lost at a time when the abundance of the average transcript, in contrast, was increasing.

The temporal pattern of IGF-II gene expression early in development is consistent with a putative role in neuromuscular synapse formation and elimination. Applicant observed that the IGF-II gene is expressed in limb buds from 14-day-old rat embryos, prior to the formation of synapses. The transcripts had the highest relative abundance in embryonic 16, 18, and 20-day-old rats during the known accumulation of multiple synapses. Multiple synapses accumulate until shortly before birth (21 days), and most if not all individual muscle fibers of neonatal rats are innervated by multiple motor axons. This mechanism may ensure innervation of all available targets. Thereafter, a postnatal pruning process follows to eliminate superfluous synapses. Applicant found that the elimination followed the reduction in IGF-II mRNA levels.

Applicant also tested the hypothesis that maturation of synapses may lead to down regulation of IGF-II mRNA levels in muscle. If the hypothesis were correct, transection of the sciatic nerve should remove the inhibition and IGF-II mRNA levels should again increase in denervated muscle. FIG. 11 shows the results of the experiment. The sciatic nerve was transected high up in only the left hip, or both the left and right hips, of anesthetized 14-day-old littermates. After 10 days, RNA was isolated from both the left and right calf muscles. The RNA (40 ug per lane) was analyzed by Northern blot as in FIG. 10. The autoradiogram shows left-right samples from the same animal adjacent to one another. LI, left intact; RI, right intact; LO, left denervated; RO, right denervated; U, unilateral transection; B, bilateral transection. Ethidium bromide staining confirmed that equivalent amounts of undegraded RNA were present in each lane.

The results show that following unilateral denervation, the relative abundance of IGF-II transcripts was increased in RNA from the denervated left, but not intact right calf muscles: 4.17±1.4, intact muscles; 17.50±5.27, denervated muscles. $P<0.01$ in one-tailed test (relative AUC values, means±SD, N=3. Moreover, following bilateral transection, IGF-II levels were elevated in both left and right denervated leg muscles. The level of significance was even greater when a comparison test was made between all intact vs all denervated samples: 6.84±3.04 (N=7), intact; 14.65±3.83 (N=9), denervated; $P<0.005$. Denervation was found to prevent the down regulation of IGF-II gene expression that is associated with development. It also removed inhibition of gene expression because transcript levels rose from barely to readily detectible levels in muscles of 4-month or older rats following sciatic nerve transection in other experiments. The same samples as described in FIG. 11 were loaded onto slot blots (8 ug per slot) and hybridized to $^{32}$P-labeled oligo(dT). The IGF-II mRNA is selectively increased in RNA from denervated muscle because there was no statistical difference in the relative amounts of oligo(dT) that were hybridized to RNA from denervated and intact muscles: 122±8 (N=7), intact; 118±6 (N=9), denervated. These are relative AUC values (means±SEM).

None of the forgoing data show whether exogenous IGFs can prevent or repair neuropathy, particularly diabetic neuropathy. Applicant has found that locally infused IGF-II can prevent impairment of conduction velocity in diabetic rats (Table 1). Rats were randomly assigned to treatment groups. Some rats were made diabetic by the procedure described above under FIG. 7. Subgroups of nondiabetic and diabetic rats were implanted with miniosmotic pumps which released either vehicle, IGF-II or insulin through a catheter anchored close to the sciatic nerve about mid-thigh in the left hind limb. After 1 week, the conduction velocity was measured in both the left and right sciatic nerves.

Comparisons were made between different treatment groups of rats. In Table 1 Part A the conduction velocity was significantly reduced in diabetic relative to nondiabetic Lewis rats without pumps. It was also significantly reduced in diabetic relative to nondiabetic rats treated with vehicle; this was evident whether comparisons were made between left or right sides. In contrast, the decline in conduction velocity was prevented in the left but not right nerve of diabetic rats treated with IGF-II. This showed that 100 ug/ml IGF-II acted locally only near its site of infusion, and, surprisingly, that the epineurium was not an impenetrable barrier to IGF-II. The mechanism by which IGF-II crosses the epineurium is not known. The effect of IGF-II, however, was not replicated by local infusion of a similar concentration of insulin.

A pairwise comparison of the difference in conduction velocity between left and right nerves of individual rats was conducted. The virture of this test is that each rat serves as its own internal control, and avoids the potential for individual differences between animals. In nondiabetic Sprague-Dawley rats, differences in conduction velocity between left and right nerves were not encountered, whether miniosmotic pumps were implanted or not (Table I, Part B). Likewise, left-right nerve differences were not observed in vehicle-treated Lewis rats, whether diabetic or not, or in insulin-treated rats (Table I, Part A).

Significant differences, however, were observed in conduction velocity between left and right nerves of both Lewis and Sprague-Dawley rats treated with vehicle vs 100 or 300 $\mu$g/ml IGF-II, respectively, as shown in FIG. 12. The positive differences showed that the conduction velocity was in both Lewis and Sprague-Dawley rats faster in the left nerve, which was closest to the site of IGF-II infusion. These results provide the first demonstration that IGFs can prevent neuropathy, particularly diabetic neuropathy.

A distinguishing feature of Applicant's theory, from other theories for pathogenesis of diabetic neuropathy, is that neuropathy is not the secondary consequence of hyperglycemia. Applicant's theory predicts that IGFs could prevent neuropath despite hyperglycemia, and this theory was tested. It was found that IGFs could prevent neuropathy despite hyperglycemia. Blood samples were withdrawn on post-surgical Days 1 and 7 from most of the rats shown in Table 1 and FIG. 12. Plasma glucose was measured by the glucose oxidase and peroxidase procedure, using commercially available Kit 510 from Sigma Chemical Co. Comparisons were made between groups matched for the presence or absence of pumps, type and duration of treatment, and rat strain (Table 2). Marked hyperglycemia was found in all diabetic rats, whether implanted with pumps or not. The glucose concentration was significantly elevated in diabetic rats treated with IGF-II relative to nondiabetic rats treated with vehicle; this was observed in both Sprague-Dawley and Lewis animals. Moreover, the degree of hyperglycemia was not reduced in IGF-II treated relative to vehicle-treated diabetic rats. These results show that the local infusion of IGF-II did not reduce hyperglycemia. Moreover, a similar concentration of locally infused insulin did not diminish hyperglycemia in Lewis rats (Table 2, Part A). This further reduced the likelihood that infused IGF-II might reduce hyperglycemia by cross-occupation of insulin receptors. Thus, this test validates another important prediction of Applicant's hypothesis. The results show that IGF-II can be used to prevent neuropathy, despite hyperglycemia. The results suggest IGF-II can be useful for treatment of diabetic neuropathy independent of treatment with insulin or hypoglycemia agent. It cannot be known whether IGF-I would be useful, and separate test is needed.

Heretofore, the in vitro data and Hannson et al (1986) did not reveal whether exogenous IGFs can increase regeneration in vivo. Applicant has studied whether infused IGF-II can increase the regeneration distance in crushed sciatic nerves of rats (Table 3). Applicant finds that 1 ug/ml IGF-II can increase regeneration distance. Rats (12-weeks-old) were randomly assorted into groups. Sciatic nerves were crushed with a jeweler's forceps (0.5 mm) at mid-thigh, and the segment 2 cm below the site of crush was frozen. This method largely eliminates Schwann and other cells in the nerve so that one might sequentially add back and determine the relative contribution of various factors to regeneration. The site of crush was labeled with a tiny suture passed through surrounding connective tissue. The distal end of the frozen nerve segment was transected and ligated. Miniosmotic pumps were implanted, and pump catheters released either RPMI 1640 vehicle or 1 or 10 $\mu$g/ml IGF-II close to the site of crush. At 4 days post-crush, the regeneration distance into the frozen segment below the site of crush was measured by a pinch reflex test. Successive proximal 0.5 mm pinches, beginning from the most distal end of the frozen segment, locates the position of regenerating sensory axons by a reflex contracture of body musculature. The regeneration distance was significantly increased by 1 and 10 $\mu$g/ml IGF-II vs vehicle.

The increase in regeneration distance caused by IGF-II in vivo was only a few mm (Table 3), and does not reveal whether the invention has any utility, because it does not reveal whether the rate of regeneration is increased. It is even possible IGFs cause the axons to temporarily sprout for a few mm, then retract later. Consider two automobiles traveling a distance of 100 miles. If auto A were given a few feet head start, but auto A and B traveled at the same rate of 20 mph, auto A would reach its distance at a time not very different from auto B. Likewise a few mm head start in nerve regeneration would not be useful. What is critical to know is whether IGFs can increase the rate of nerve regeneration. Human nerves regenerate at a rate of about 1 mm/day, and it would take more than a year to grow a distance of a meter. A doubling of the rate would save half a year, and could be significant in preventing atrophy and degeneration of end organs, and diminishing the potential for permanent paralysis. In FIG. 13, rats (12-weeks-old) were randomly assorted into groups. Sciatic nerves were crushed and frozen as described for Table 3. Miniosmotic pumps were implanted, and pump catheters released either RPMI 1640 vehicle (open circles) or 1 ug/ml IGF-II (solid circles) close to the site of crush. At various post-surgical times up to 6 days, regeneration distance into the frozen segment below the site of crush was measured by the pinch reflex test. The regeneration distance was significantly increased by IGF-II vs vehicle. For example, at Days 4 and 6, P<0.001.

Linear regression was analyzed by computer using the method of least squares for best fit. The data for the control group fit the equation Y=0.65+1.31X (r=0.98), whereas the data for the IGF-II treated group fit the equation Y=−1.47+1.92X (r=0.99). Y is the regeneration distance in mm, X is time in days, and r is the coefficient of correlation. There was little difference in the onset of regeneration, and IGF-II increased the regeneration rate by 47%. The coefficients of correlation showed that both sets of data fit a straight line model very closely. These data provide the first demonstration that IGFs can increase the rate of nerve regeneration, and may have utility.

Applicant's work further suggests that multiple neurotrophic factors may act in concert on the afflicted population of neurons. Distinct receptors for insulin, IGFs, and NGF can be found on the same cell and it now appears that each liquid acts through its own receptor at physiological concentrations. Primary cultures of sensory, sympathetic and spinal cord neurons display a pattern of neurite growth response which indicates these factors are acting on the same or overlapping populations of neurons. Moreover, these factors appear to be sharing a common mechanisms. Although prior in vitro art did not make in vivo utility obvious, in light of the disclosure of this patent application, a person of ordinary skill may now readily determine effective doses and routes of administration through routine in vivo studies with IGFs.

While this discussion is largely centered on insulin, IGFs, protein kinase C activators and NGF, considered alone, or in various combinations and permutations, applicant's paradigm does not exclude the participation of other neurotrophic agents. Those skilled in this art will appreciate that such changes can be made without departing from the scope and spirit of this patent disclosure.

Thus having disclosed this invention, what is claimed is:

1. A method for treating the peripheral nervous system of a postnatal mammal suffering from a diabetic neuropathic condition comprising administering to the mammal a polypeptide nerve growth factor (NGF) in an amount effective to ameliorate the diabetic neuropathic condition.

2. The method of claim 1, wherein the factor is administered at a serum concentration from about 0.01 nM to about 1 $\mu$M.

3. The method of claim 1, wherein the mammal is a human.

* * * * *